United States Patent
Lymperopoulos et al.

(10) Patent No.: US 10,172,907 B2
(45) Date of Patent: Jan. 8, 2019

(54) COMPOSITIONS COMPRISING β-ARRESTIN 1 AND METHODS OF USE THEREOF FOR THERAPEUTIC MODULATION OF ALDOSTERONE LEVELS IN HEART DISEASE

(75) Inventors: Anastasios Lymperopoulos, Fort Lauderdale, FL (US); Walter J. Koch, Philadelphia, PA (US)

(73) Assignees: NOVA SOUTHEASTERN UNIVERSITY, Fort Lauderdale, FL (US); THOMAS JEFFERSON UNIVERSITY, Philadelphia, PA (US)

( * ) Notice: Subject to any disclaimer, the term of this patent is extended or adjusted under 35 U.S.C. 154(b) by 169 days.

(21) Appl. No.: 13/877,955

(22) PCT Filed: Oct. 5, 2011

(86) PCT No.: PCT/US2011/054955
§ 371 (c)(1),
(2), (4) Date: Jun. 21, 2013

(87) PCT Pub. No.: WO2012/048022
PCT Pub. Date: Apr. 12, 2012

(65) Prior Publication Data
US 2013/0274191 A1    Oct. 17, 2013

Related U.S. Application Data

(60) Provisional application No. 61/389,819, filed on Oct. 5, 2010.

(51) Int. Cl.
| | |
|---|---|
| *A61P 9/04* | (2006.01) |
| *A61K 38/17* | (2006.01) |
| *A61K 31/41* | (2006.01) |
| *A61K 38/08* | (2006.01) |
| *A61K 31/4184* | (2006.01) |
| *C07K 14/47* | (2006.01) |

(52) U.S. Cl.
CPC ............ *A61K 38/085* (2013.01); *A61K 31/41* (2013.01); *A61K 31/4184* (2013.01); *A61K 38/1709* (2013.01); *A61P 9/04* (2018.01); *C07K 14/4703* (2013.01)

(58) Field of Classification Search
None
See application file for complete search history.

(56) References Cited

U.S. PATENT DOCUMENTS

| | | |
|---|---|---|
| 2008/0167294 A1 | 7/2008 | Meyers et al. |
| 2009/0227507 A1 | 9/2009 | Rodgers et al. |
| 2010/0166837 A1 | 7/2010 | Matsoukas |

OTHER PUBLICATIONS

Lymperopoulos et al, 2009. Conference Abstract P106 from the Basic Cardiovascular Sciences Conference 2009—Molecular Mechanisms of Cardiovascular Disease, Jul. 20-23, 2009. Published in Circulation Research, Sep. 25, 2009. vol. 105(7): E31.*
Dery et al, 1999. J Biol Chem. 274(26): 18524-18535.*
Jugdutt, 2006. Vascular Health and Risk Management. 2(2): 125-138.*
Mo et al, 2008. Molecular Cell. 31: 695-707.*
Thomas S, Rich MW. Epidemiology, pathophysiology, and prognosis of heart failure in the elderly. Heart Fail Clin 2007;3:381-7.
Kaye DM, Krum H. Drug discovery for heart failure: a new era or the end of the pipeline? Nat Rev Drug Disc 2007;6:127-9.
Weber KT. Aldosterone in congestive heart failure. N Engl J Med 2001;345:1689-97.
Connell JM, Davies E. The new biology of aldosterone. J Endocrinol 2005;186:1-20.
Marney AM, Brown NJ. Aldosterone and end-organ damage. Clin Sci (Lond) 2007;113:267-78.
Zhao W, Ahokas RA, Weber KT, Sun Y. ANG II-induced cardiac molecular and cellular events: role of aldosterone. Am J Physiol Heart Circ Physiol 2006;291:H336-43.
Swedberg K, Eneroth P, Kjekshus J, Wilhelmsen L. Hormones regulating cardiovascular function in patients with severe congestive heart failure and their relation to mortality. CONSENSUS Trial Study Group. Circ 1990;82:1730-6.
Rouleau JL, Packer M, Moyé L, de Champlain J, Bichet D, Klein M, Rouleau JR, Sussex B, Arnold JM, Sestier F. Prognostic value of neurohumoral activation in patients with an acute myocardial infarction: effect of captopril. J Am Coll Cardiol 1994;24:583-91.
Pitt B, Remme W, Zannad F, Neaton J, Martinez F, Roniker B, Bittman R, Hurley S, Kleiman J, Gatlin M. Eplerenone, a selective aldosterone blocker, in patients with left ventricular dysfunction after myocardial infarction. N Engl J Med 2003;348:1309-21.
Pitt B, Zannad F, Remme WJ, Cody R, Castaigne A, Perez A, Palensky J, Wittes J. The effect of spironolactone on morbidity and mortality in patients with severe heart failure. Randomized Aldactone Evaluation Study Investigators. N Engl J Med 1999;341:709-17.

(Continued)

*Primary Examiner* — Zachary C Howard
(74) *Attorney, Agent, or Firm* — Fleit Gibbons Gutman Bongini & Bianco PL

(57) ABSTRACT

The invention concerns the contribution of elevated levels of circulating alsoterone to heart disease and other hyperaldosteronic conditions. Since activation of β-arrestin 1(βarr1) by the Angiotensin II (AngII) type 1 receptor ($AT_1R$) mediates AngII-induced aldosterone production, β-arrestin 1(βarr1) is a therapeutic target for heart disease. The invention provides a βarr1 protein fragment comprising the C-terminus of βarr1 (βarr1ct; SEQ ID NO:3), compositions containing this protein fragment, and methods of using this protein fragment to reduce elevated levels of aldosterone in heart disease and other hyperaldosteronic conditions by inhibition of β-arrestin 1(βarr1). These compositions and methods are of therapeutic benefit in chronic heart failure and progression to heart failure after myocardial infarction (MI). Additionally, the invention provides an AngII peptide analog (SEQ ID NO:4), compositions containing this analog, and methods of using this analog for stimulation of βarr1 activity and aldosterone production.

5 Claims, 10 Drawing Sheets
Specification includes a Sequence Listing.

(56) References Cited

OTHER PUBLICATIONS

De Gasparo M, Catt KJ, Inagami T, Wright JW, Unger T. International union of pharmacology. XXIII. The angiotensin II receptors. Pharmacol Rev 2000;52:415-72.
Lefkowitz RJ, Shenoy SK. Transduction of Receptor Signals by B-Arrestins. Science 2005;308:512-7.
DeWire SM, Ahn S, Lefkowitz RJ, Shenoy SK. Beta-arrestins and cell signaling. Annu Rev Physiol 2007;69:483-510.
Lymperopoulos A, Rengo G, Zincarelli C, Kim J, Soltys S, Koch WJ. An adrenal β-arrestin 1-mediated signaling pathway underlies angiotensin II-induced aldosterone production in vitro and in vivo. Proc Natl Acad Sci USA 2009;106:5825-30.
Lymperopoulos A, Rengo G, Funakoshi H, Eckhart AD, Koch WJ. Adrenal GRK2 upregulation mediates sympathetic overdrive in heart failure. Nat Med 2007;13:315-23.
Lymperopoulos A, Rengo G, Zincarelli C, Soltys S, Koch WJ. Modulation of Adrenal Catecholamine Secretion by In Vivo Gene Transfer and Manipulation of G Protein-coupled Receptor Kinase-2 Activity. Mol Ther 2008;16:302-7.
Wan W, Powers AS, Li J, Ji L, Erikson JM, Zhang JQ. Effect of Post-Myocardial Infarction Exercise Training on the Renin-Angiotensin-Aldosterone System and Cardiac Function. Am J Med Sci 2007;334:265-73.
Ishiyama Y, Gallagher PE, Averill DB, Tallant EA, Brosnihan KB, Ferrario CM. Upregulation of Angiotensin-Converting Enzyme 2 After Myocardial Infarction by Blockade of Angiotensin II Receptors. Hypertension 2004;43:970-6.
Mihailidou AS, Mardini M, Funder JW, Raison M. Mineralocorticoid and Angiotensin Receptor Antagonism During Hyperaldosteronemia. Hypertension 2002;40:124-9.
Rengo G, Lymperopoulos A, Zincarelli C, Donniacuo M, Soltys S, Rabinowitz JE, Koch WJ. Myocardial adeno-associated virus serotype 6-betaARKct gene therapy improves cardiac function and normalizes the neurohormonal axis in chronic heart failure. Circ 2009;119:89-98.
Shibata R, Ouchi N, Ito M, Kihara S, Shiojima I, Pimentel DR, Kumada M, Sato K, Schiekofer S, Ohashi K, Funahashi T, Colucci WS, Walsh K. Adiponectin-mediated modulation of hypertrophic signals in the heart. Nat Med 2004;10:1384-9.
McMurray JJ. Angiotensin inhibition in heart failure. J Renin Angiotensin Aldosterone Syst 2004;5 Suppl. 1:S17-S22.
Diez J. Review of the molecular pharmacology of Losartan and its possible relevance to stroke prevention in patients with hypertension. Clin Ther 2006;28:832-48.
Qin W, Rudolph AE, Bond BR, Rocha R, Blomme EA, Goellner JJ, Funder JW, McMahon EG. Transgenic model of aldosterone-driven cardiac hypertrophy and heart failure. Circ Res 2003;93:69-76.
Rockman HA, Choi DJ, Rahman NU, Akhter SA, Lefkowitz RJ, Koch WJ. Receptor-specific in vivo desensitization by the G protein-coupled receptor kinase-5 in transgenic mice. Proc Natl Acad Sci USA 1996;93:9954-9.
Kobori H, Nangaku M, Navar LG, Nishiyama A. The intrarenal renin-angiotensin system: from physiology to the pathobiology of hypertension and kidney disease. Pharmacol Rev 2007;59:251-87.

Silvestre JS, Heymes C, Oubénaïssa A, Robert V, Aupetit-Faisant B, Carayon A, Swynghedauw B, Delcayre C. Activation of cardiac aldosterone production in rat myocardial infarction: effect of angiotensin II receptor blockade and role in cardiac fibrosis. Circ 1999;99:2694-701.
Rockman HA, Koch WJ, Lefkowitz RJ. Seven-transmembrane-spanning receptors and heart function. Nature 2002;415:206-12.
Conner DA, Mathier MA, Mortensen RM, Christe M, Vatner SF, Seidman CE, Seidman JG. beta-Arrestin1 knockout mice appear normal but demonstrate altered cardiac responses to beta-adrenergic stimulation. Circ Res 1997;81:1021-6.
Nehme JA, Lacolley P, Labat C, Challande P, Robidel E, Perret C, Leenhardt A, Safar ME, Delcayre C, Milliez P. Spironolactone improves carotid artery fibrosis and distensibility in rat post-ischaemic heart failure. J Mol Cell Cardiol 2005;39:511-9.
Benetos A, Lacolley P, Safar ME. Prevention of aortic fibrosis by spironolactone in spontaneously hypertensive rats. Arterioscler Thromb Vasc Biol 1997;17:1152-6.
Borghi C, Boschi S, Ambrosioni E, Melandri G, Branzi A, Magnani B. Evidence of a partial escape of reninangiotensin-aldosterone blockade in patients with acute myocardial infarction treated with ACE inhibitors. J Clin Pharmacol 1993;33:40-5.
Struthers AD. Aldosterone escape during ACE inhibitor therapy in chronic heart failure. Eur Heart J 1995;16 (Supp N): 103-6.
Violin JD, Lefkowitz RJ. Beta-arrestin-biased ligands at seven-transmembrane receptors. Trends Pharmacol Sci 2007;28:416-22.
Neubig RR. Missing Links: Mechanisms of Protean Agonism. Mol Pharmacol 2007;71:1200-2. Pitt B, et al. J. Am. Coll. Cardiol. (2005) 46: 425-431.
Pitt B, et al. J. Am. Coll. Cardiol. (2005) 46: 425-431.
Rainey WE, et al. Mol. Cell. Endocrinol. (2004) 228: 23-38.
Oro C, et al. Pharmacol. Ther. (2007) 113: 210-226.
Luttrell LM, Gesty-Palmer D. Pharmacol. Rev. (2010) 62: 305-330.
Rajagopal S, et al. Nat. Rev. Drug Discov. (2010) 9: 373-386.
Kenakin T, Miller LJ. Pharmacol. Rev. (2010) 62: 265-304.
Massie BM, et al. N. Engl. J. Med. (2008) 359: 2456-2467.
Written Opinion of the International Search PCT/US2011/054955, filed Feb. 5, 2012.
International Preliminary Report for PCT/US2011/054955, filed Feb. 5, 2012.
Initial Publication WO 2012048022 published Apr. 12, 2012.
Lymperopoulos et al., An adrenal beta-arrestin 1 mediated signaling pathway underline angiotensinn . . . , Natl Acad Sci USA 2009, vol. 106(14), p. 5825-30, EPub 2009 Abstract p. 5825.
Kern et al., Arrestin2/Clathrin Interaction is regulated by Key N. and Clerminal Regions in Arrestin2+, Biochemistry 2009, vol. 48(30), p. 7190-7200.
UniProt_D3ZMC2, Uncharacterized protein, last modified, Apr. 20, 2010, online, www.uniprot.org/uniprot/D3ZMC2, 361-410.
UniProt_P71025, HTH-type transcriptional regulator CzcR, Last modified: Jul. 1, 1997, online www.uniprot.org/uniprot/P71025, 243-249.
Ryan T. Kendall et al., The B-Arrestin Pathway-selective Type 1A Angiotensin Receptor . . . , Journal of Biological Chemistry, vol. 286 No. 22, pp. 19880 19891 Jun. 3, 2011.
Lymperopoulos et al., Adrenal beta-arrestin 1 inhibition in Vivo Attenuates Post-Myocardial Infarction Progression to Heart Failure and Adverse remodeling via reduction of circulating Aldosterone levels, Journal of the American College of Cardiology, Apr. 3, 2012.

* cited by examiner

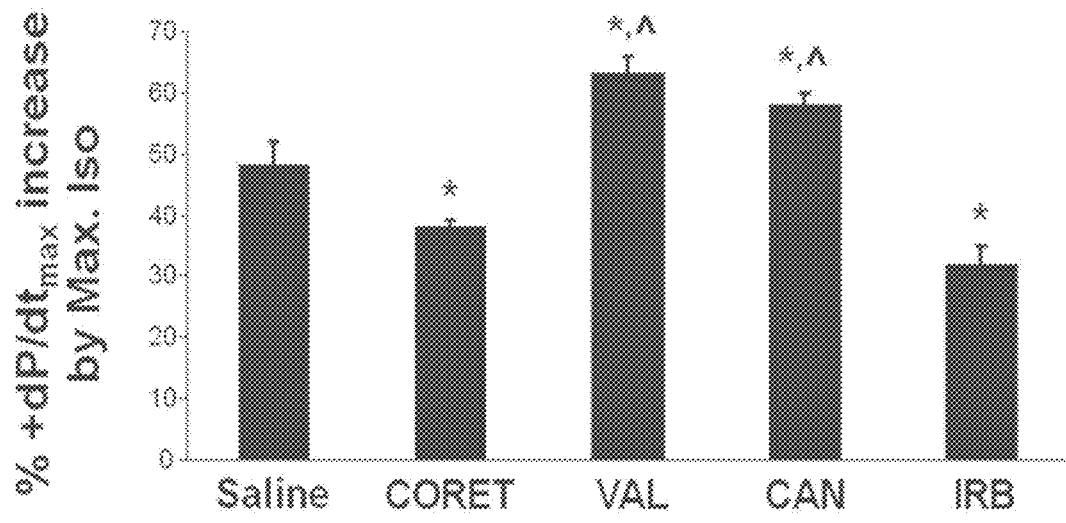
FIG 5
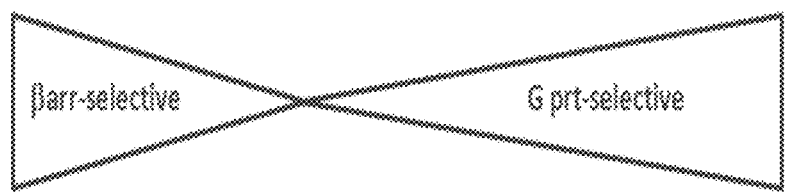
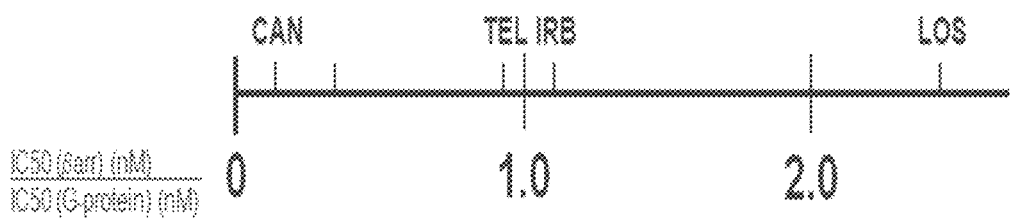
FIG 6

FIG 7A
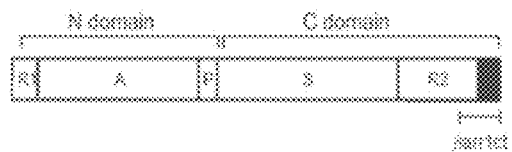
FIG 7B
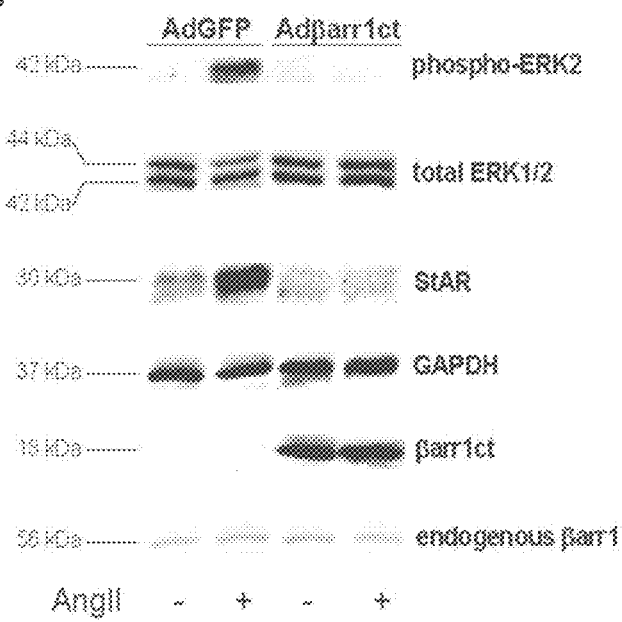
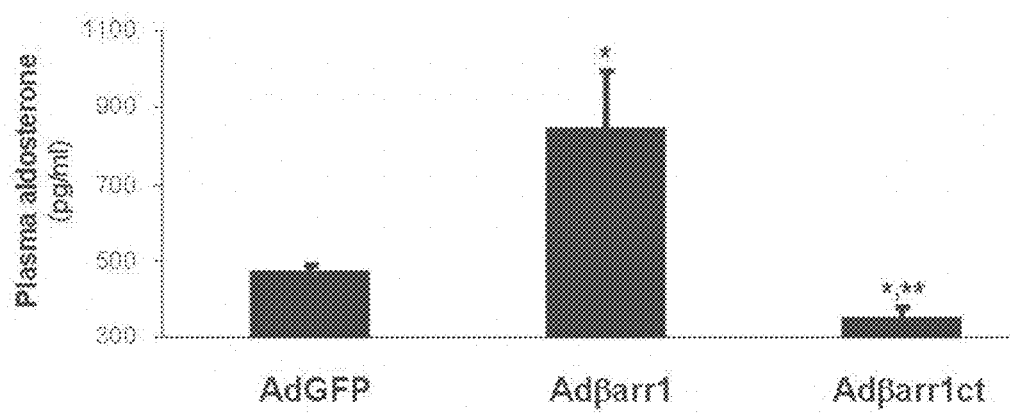
FIG 9

FIG 8A
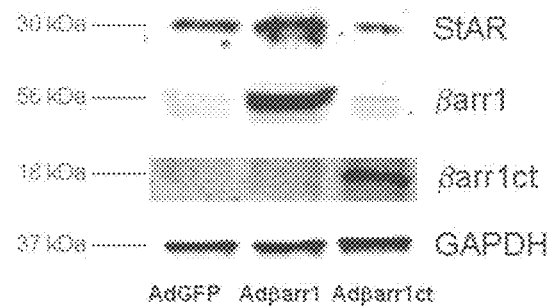
FIG 8B
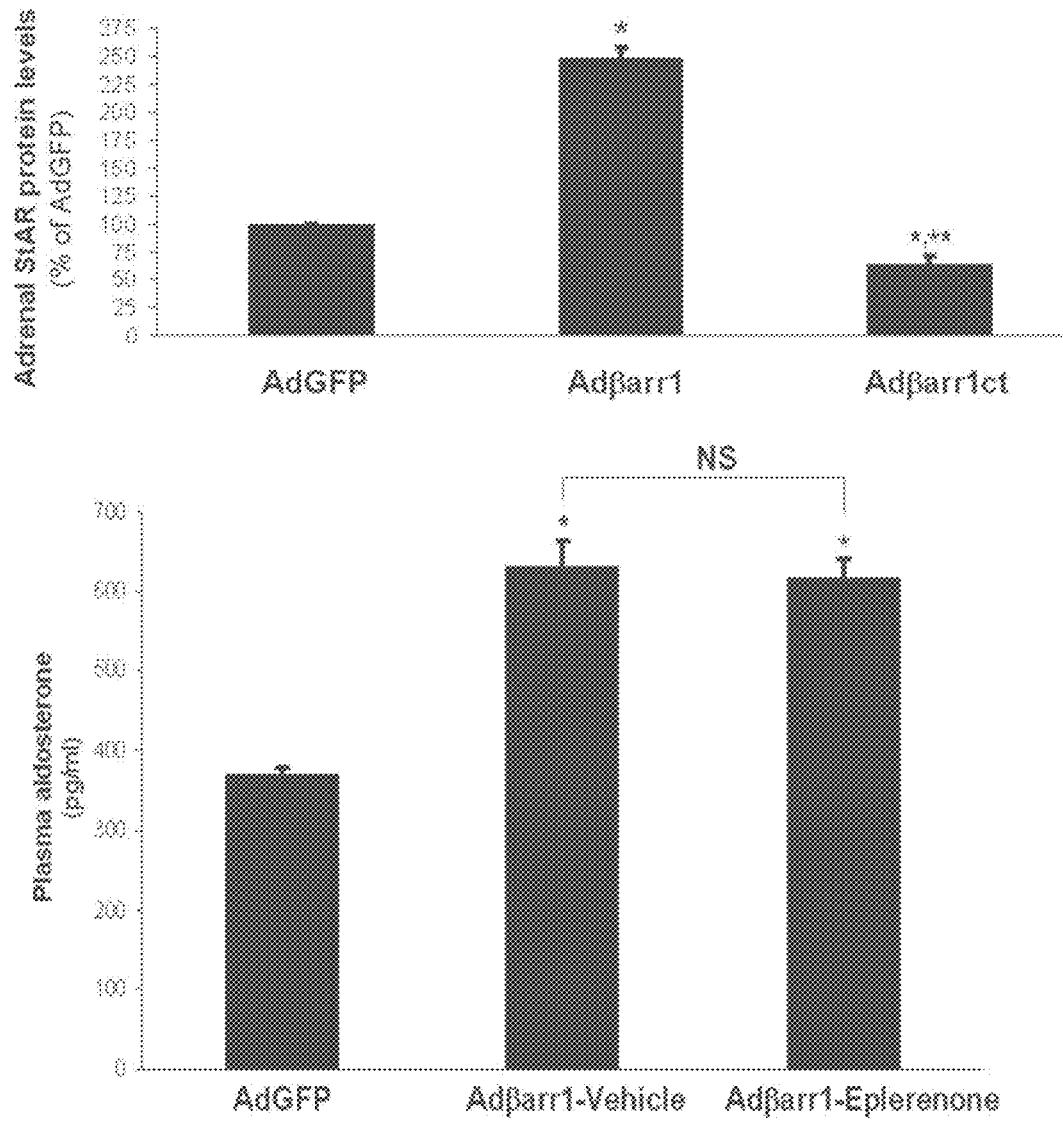
FIG 11

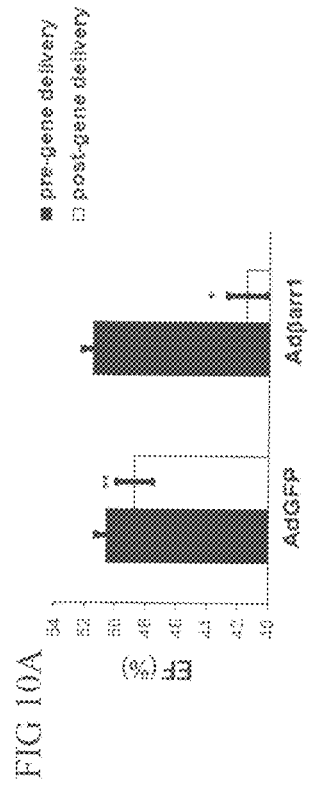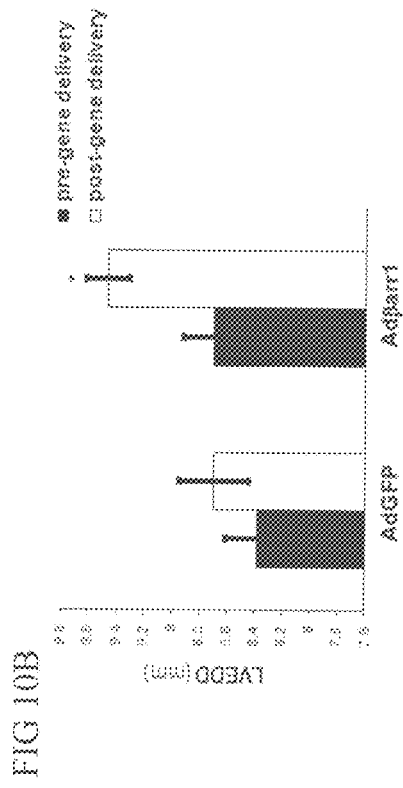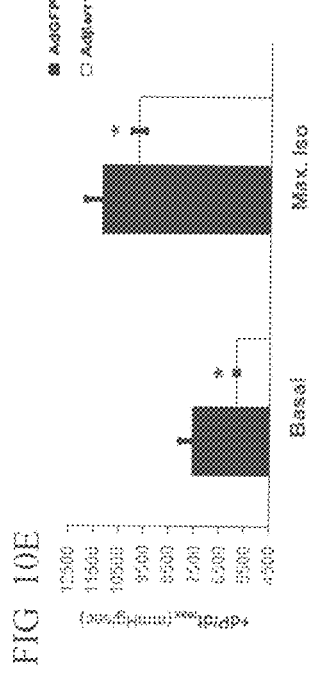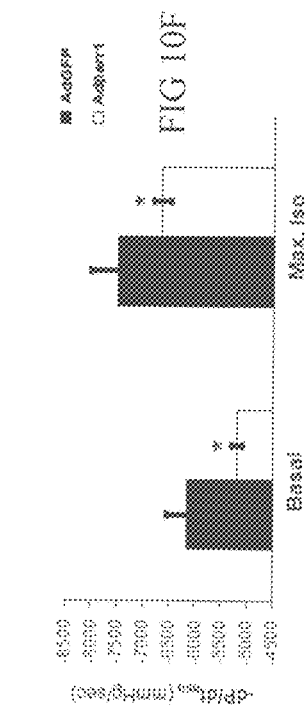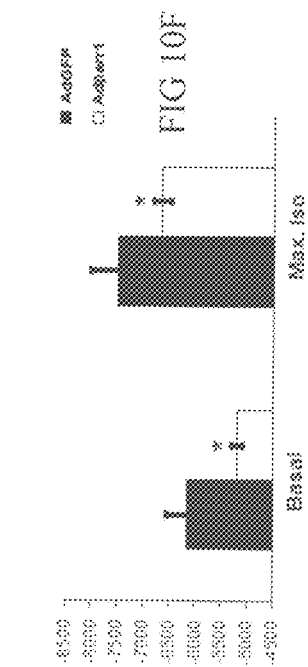

SEQUENCE LISTING

<160> NUMBER OF SEQ ID NOS: 16

<210> SEQ ID NO 1
<211> LENGTH: 1357
<212> TYPE: DNA
<213> ORGANISM: Rattus norvegicus

<400> SEQUENCE: 1

```
cgccgccgcg gacctccctg cggccgccgc ggaccatggg cgacaaaggg acacgagtgt      60
tcaagaaggc aagccccaat ggaaagctca ccgtctacct gggaaagcgg gactttgtgg     120
accacattga cctggtggac cccgtggatg gcgtggtcct ggtggatcct gagtatctca     180
aagaaaggcg agtctacgtg acactgacct gcgccttccg gtatggccgg gaagacctgg     240
atgtcttggg tctgactttt cgcaaagacc tgtttgtggc taacgtgcag tccttcccac     300
cggcccctga ggacaagaag ccactgactc ggctacaaga gcgactcatc aagaagctgg     360
gcgagcatgc ctacccttc accttgaga tcccgccaaa ccttccgtgc tcagtcacat      420
tgcaacctgg gcctgaggac acagggaagg cctgcggtgt ggattatgaa gtgaaagcct     480
tctgtgctga gaacctggag gagaagatcc acaaaaggaa ttctgtgcgg ctagtcatcc     540
ggaaggttca atatgcccct gagaggcctg gccctcagcc cacggctgag accaccagac     600
agttcctcat gtcggacaag cccctgcacc ttgaggcatc tctggataag gagatctatt     660
atcatggaga acccatcagc gtcaatgtcc atgtcaccaa caacaccaac aagactgtga     720
agaagatcaa gatctcggtg cgccagtatg cagacatctg tctcttcaac acagctcagt     780
acaagtgccc agtggccatg gaggaagctg atgatactgt ggcacccagc tcaacattct     840
gcaaggtcta cactgact cccttcctgg caaacaacag agagaagcgg gggcttgccc     900
```

-continued

```
tcgacgggaa gctcaagcat gaagacacaa atctggcttc cagcactctg ttgcgggaag    960
gcgccaaccg tgaaatcctg ggtatcattg tttcctacaa agtcaaagtg aagctggtgg   1020
tgtcccgggg cggcctgttg ggagaccttg catccagtga tgtggctgtg aactgccct    1080 ttaccttaat gcaccccaag cctaaagagg agccccaca tcgggaagtt ccagagagcg    1140
agactccagt agacaccaat ctcatagagc ttgacaccaa tgatgacgac attgtgtttg   1200
aggactttgc tcgtcagcgg ctgaaaggca tgaaggatga caaggacgaa gaggatgatg   1260
gcaccggctc tccacacctc aacaacagat agactggggc cagcctcagc ccagcagctc   1320
caggttcact ctcgcactcg gatgctttct cgtctct                            1357
```

<210> SEQ ID NO 2
<211> LENGTH: 418
<212> TYPE: PRT
<213> ORGANISM: Rattus norvegicus

<400> SEQUENCE: 2

Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
            20                  25                  30

Leu Val Asp Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125

Leu Gln Pro Gly Pro Glu Asp Thr Gly Lys Ala Cys Gly Val Asp Tyr
    130                 135                 140

Glu Val Lys Ala Phe Cys Ala Glu Asn Leu Glu Glu Lys Ile His Lys
145                 150                 155                 160

Arg Asn Ser Val Arg Leu Val Ile Arg Lys Val Gln Tyr Ala Pro Glu
                165                 170                 175

Arg Pro Gln Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
        195                 200                 205

Tyr His Gly Glu Pro Ile Ser Val Asn Val His Val Thr Asn Asn Thr
    210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
                245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
        275                 280                 285

Leu Asp Gly Lys Leu Lys His Glu Asp Thr Asn Leu Ala Ser Ser Thr

```
                290                 295                 300
Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Leu Leu Gly
                325                 330                 335

Asp Leu Ala Ser Ser Asp Val Ala Val Glu Leu Pro Phe Thr Leu Met
                340                 345                 350

His Pro Lys Pro Lys Glu Glu Pro Pro His Arg Glu Val Pro Glu Ser
                355                 360                 365

Glu Thr Pro Val Asp Thr Asn Leu Ile Glu Leu Asp Thr Asn Asp Asp
                370                 375                 380

Asp Ile Val Phe Glu Asp Phe Ala Arg Gln Arg Leu Lys Gly Met Lys
385                 390                 395                 400

Asp Asp Lys Asp Glu Glu Asp Asp Gly Thr Gly Ser Pro His Leu Asn
                405                 410                 415

Asn Arg

<210> SEQ ID NO 3
<211> LENGTH: 50
<212> TYPE: PRT
<213> ORGANISM: Rattus norvegicus

<400> SEQUENCE: 3

Glu Thr Pro Val Asp Thr Asn Leu Ile Glu Leu Asp Thr Asn Asp Asp
1               5                   10                  15

Asp Ile Val Phe Glu Asp Phe Ala Arg Gln Arg Leu Lys Gly Met Lys
                20                  25                  30

Asp Asp Lys Asp Glu Glu Asp Asp Gly Thr Gly Ser Pro His Leu Asn
            35                  40                  45

Asn Arg
    50

<210> SEQ ID NO 4
<211> LENGTH: 7
<212> TYPE: PRT
<213> ORGANISM: Artificial Sequence
<220> FEATURE:
<223> OTHER INFORMATION: Angiotensin II Type-I Receptor agonist peptide

<400> SEQUENCE: 4

Arg Val Tyr Cys His Pro Leu
1               5

<210> SEQ ID NO 5
<211> LENGTH: 20
<212> TYPE: DNA
<213> ORGANISM: Artificial Sequence
<220> FEATURE:
<223> OTHER INFORMATION: primer sequence for PCR

<400> SEQUENCE: 5
gtccacgagg tgacaaaggt                                           20

<210> SEQ ID NO 6
<211> LENGTH: 20
<212> TYPE: DNA
<213> ORGANISM: Artificial Sequence
<220> FEATURE:
<223> OTHER INFORMATION: primer sequence for PCR

<400> SEQUENCE: 6
```
catcttttcc aggaggtcca                    20

<210> SEQ ID NO 7
<211> LENGTH: 20
<212> TYPE: DNA
<213> ORGANISM: Artificial Sequence
<220> FEATURE:
<223> OTHER INFORMATION: primer sequence for PCR

<400> SEQUENCE: 7
caccccttct gcgttgtatt                    20

<210> SEQ ID NO 8
<211> LENGTH: 20
<212> TYPE: DNA
<213> ORGANISM: Artificial Sequence
<220> FEATURE:
<223> OTHER INFORMATION: primer sequence for PCR

<400> SEQUENCE: 8
ttgaccctaa ccaaggatgc                    20

<210> SEQ ID NO 9
<211> LENGTH: 22
<212> TYPE: DNA
<213> ORGANISM: Artificial Sequence
<220> FEATURE:
<223> OTHER INFORMATION: primer sequence for PCR

<400> SEQUENCE: 9
tgcctgcacc tttgtgatat cg                 22

<210> SEQ ID NO 10
<211> LENGTH: 20
<212> TYPE: DNA
<213> ORGANISM: Artificial Sequence
<220> FEATURE:
<223> OTHER INFORMATION: primer sequence for PCR

<400> SEQUENCE: 10
catggcagga caatcgaacc                    20

<210> SEQ ID NO 11
<211> LENGTH: 17
<212> TYPE: DNA
<213> ORGANISM: Artificial Sequence
<220> FEATURE:
<223> OTHER INFORMATION: primer sequence for PCR

<400> SEQUENCE: 11
catcctggac aacctgc                       17

<210> SEQ ID NO 12
<211> LENGTH: 17
<212> TYPE: DNA
<213> ORGANISM: Artificial Sequence
<220> FEATURE:
<223> OTHER INFORMATION: primer sequence for PCR

<400> SEQUENCE: 12
taggtccgaa ccttgcc                       17

<210> SEQ ID NO 13
<211> LENGTH: 20
<212> TYPE: DNA

```
<213> ORGANISM: Artificial Sequence
<220> FEATURE:
<223> OTHER INFORMATION: primer sequence for PCR

<400> SEQUENCE: 13
tcaagaacga aagtcggagg                                                   20

<210> SEQ ID NO 14
<211> LENGTH: 19
<212> TYPE: DNA
<213> ORGANISM: Artificial Sequence
<220> FEATURE:
<223> OTHER INFORMATION: primer sequence for PCR

<400> SEQUENCE: 14
ggacatctaa gggcatcac                                                    19

<210> SEQ ID NO 15
<211> LENGTH: 7
<212> TYPE: PRT
<213> ORGANISM: Artificial Sequence
<220> FEATURE:
<223> OTHER INFORMATION: Angiotensin II Type-I Receptor agonist peptide

<400> SEQUENCE: 15

Arg Val Tyr Met His Pro Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Angiotensin II Type-1 Receptor analog peptide

<400> SEQUENCE: 16

Asp Arg Val Tyr Met His Pro
1               5
```

COMPOSITIONS COMPRISING β-ARRESTIN 1 AND METHODS OF USE THEREOF FOR THERAPEUTIC MODULATION OF ALDOSTERONE LEVELS IN HEART DISEASE

CROSS REFERENCE TO RELATED APPLICATIONS

This application claims the benefit of priority to U.S. Provisional Patent Application 61/389,819, filed on Oct. 5, 2010, the contents of which are herein incorporated by reference.

FIELD OF THE INVENTION

This invention generally relates to the contribution of aldosterone to heart disease and particularly to the modulation of aldosterone levels for treatment of heart disease and other hyperaldosteronic conditions. Most particularly, the invention relates to the reduction of plasma aldosterone levels via inhibition of adrenal β-arrestin 1.

BACKGROUND OF THE INVENTION

Despite recent advances in prevention and management of heart disease, death due to chronic heart failure (HF) continues to rise worldwide and new treatments are needed (Thomas, S. et al. *Heart Fail Clin* 3:381-387 2007; Kaye, D. M. et al. *Nat Rev Drug Disc* 6:127-129 2007).

Aldosterone is one of a number of hormones with detrimental effects to the myocardium, whose circulating levels are elevated in chronic heart failure (Weber, K. T. *New England Journal of Medicine* 345:1689-1697 2001) and during progression of the post-myocardial (MI) heart to heart failure. Aldosterone can contribute significantly to the morbidity and mortality of heart failure (Weber, K. T. *New England Journal of Medicine* 345:1689-1697 2001; Connel, J. M. et al. *Journal of Endocrinology* 186:1-20 2005; Marney, A. M. et al. *Clin Sci* (Lond) 113:267-278 2007). It has severely detrimental effects on the post-MI and failing myocardium, both indirect (i.e. via elevating blood pressure, enhancing sodium retention, etc.) and direct (i.e. promotion of cardiac adverse remodeling, such as cardiac fibrosis, maladaptive hypertrophy, inflammation, oxidative stress, progressive loss of cardiac function and performance etc.). (Weber, K. T. *New England Journal of Medicine* 345:1689-1697 2001; Connel, J. M. et al. *Journal of Endocrinology* 186:1-20 2005; Marney, A. M. et al. *Clin Sci* (Lond) 113:267-278 2007; Zhao, W. et al. *Am J Physiol Heart Circ Physiol* 291:H336-343 2006). Accordingly, plasma aldosterone levels are a marker of heart failure severity (Swedburg, K. et al. *CONSENSUS Trial Study Group. Circ* 82:1730-1736 1990; Rouleau, J. L. et al. *J Am Coll Cardiol* 24:583-591 1994) and aldosterone antagonists, such as spironolactone and eplerenone, have well-documented beneficial effects in heart failure constituting a significant segment of the chronic HF pharmacotherapeutic regimen (Pitt, B. et al. *New England Journal of Medicine* 348:1309-1321 2003; Pitt, B. et al. *New England Journal of Medicine* 341:709-717 1999).

Aldosterone is a mineralocorticoid produced and secreted by the cells of the zona glomerulosa of the adrenal cortex in response to either elevated serum potassium levels or to angiotensin II (AngII) acting through its type 1 receptors ($AT_1Rs$), endogenously expressed in the adrenocortical zona glomerulosa (AZG) cells (Ganguly, A. et al. *Pharmacol Rev* 46:417-447 1994). $AT_1Rs$ belong to the superfamily of G protein coupled receptors (GPCRs), and, upon agonist activation, couple to the $G_{q/11}$ family of G proteins (De Gasparo, M. et al. *Pharmacol Rev* 52:415-472 2000). Over the past few years, a number of GPCRs, including the ATiRs, have been shown to also signal through G protein-independent pathways (DeGasparo, M. et al. *Pharmacol Rev* 52:415-472 2000; Oro, C. et al. *Pharmacol Ther* 113:210-226 2007). The protein scaffolding actions of β-arrestin 1 and 2 (βaa1 and 2, also known as arrestins 2 and 3, respectively), universal receptor adapter/scaffolding proteins originally discovered as terminators of GPCR signaling, play a central role in mediating this G protein-independent signal transduction (Lefkowitz, R. J. et al. *Science* 308:512-517 2005; DeWire, S. M. et al. *Annu Rev Physiol* 69:483-510 2007).

The β-arrestin 1 (βarr1) protein regulates the function of the angiotensin II (Ang II) type 1 receptors ($AT_1Rs$) and elicits aldosterone production in response to activation by Ang II in vitro and physiologically in vivo. Normally, the $AT_1R$ produces aldosterone through activation of G-proteins, which is blocked by Paul. Paul, after terminating G-protein activation by the $AT_1R$, is capable of signaling to aldosterone production. Thus, βarr1 also results in sustained aldosterone production by Ang II in the adrenal cortex.

Accordingly, lowering aldosterone levels via adrenal βarr1 inhibition could be of enormous therapeutic benefit in post-myocardial infarction (MI) and chronic heart failure.

SUMMARY OF THE INVENTION

The β-arrestin 1 (βarr1) protein regulates the function of the angiotensin II (AngII) type 1 receptors ($AT_1Rs$), which are endogenously expressed in the zona glomerulosa cells of the adrenal cortex and elicit aldosterone production in response to activation by AngII. Normally, the $AT_1R$ produces aldosterone through activation of G-proteins, which is blocked by βarr1. However, βarr1, after terminating G-protein activation by the $AT_1R$, is capable of signaling to aldosterone production thus, also resulting in sustained aldosterone production by AngII in the adrenal cortex. Consequentially, inhibition of the adrenalcortical βarr1 activation by AngII, in addition to inhibition of G-protein activation by AngII, is needed to fully block AngII-induced adrenal aldosterone production.

Aldosterone is a mineralocorticoid whose levels are severely elevated in chronic heart failure and during progression of the post-myocardial infarction (MI) heart to heart failure. It has severely detrimental effects on the post-MI and failing myocardium, both indirect (for example, via elevating blood pressure or enhancing sodium retention) and direct (for example, promotion of cardiac adverse remodeling, such as cardiac fibrosis, maladaptive hypertrophy, and inflammation), therefore aldosterone inhibition represents a therapeutic modality in heart failure. Several aldosterone blockers, such as spironolactone and eplerenone, are part of current heart failure pharmacotherapy. Thus, lowering plasma (circulating) aldosterone levels via adrenal β-arrestin 1 inhibition could be of enormous therapeutic benefit in post-MI and chronic heart failure.

The following are examples of embodiments of the invention and do not and should not be construed as representative of the entire scope contemplated by the invention.

The invention provides compositions and methods for modulation (decrease or increase) of levels of aldosterone via controlled expression of adrenal β-arrestin 1.

Considering the therapeutic potential of reduced aldosterone levels, the invention provides a method for reducing plasma aldosterone level in a patient comprising inhibiting adrenal via adrenal β-arrestin 1 (βarr1). This method (and the following methods) can be carried out with any human or animal patient.

The invention provides a method for reducing plasma aldosterone level in a patient having a hyperaldosteronic condition comprising inhibiting adrenal via adrenal β-arrestin 1 (βarr1). Particularly, the hyperaldosteronic condition is chronic heart failure or heart failure progression post-myocardial infarction (MI).

The invention provides a protein inhibitor of adrenal β-arrestin 1 (βarr1). The protein inhibitor may cause inhibition via overexpression (of the protein inhibitor).

The invention provides a βarr1 protein fragment comprising a C-terminus of βarr1 (βarr1ct), a protein inhibitor of adrenal β-arrestin 1 (βarr1). Particularly, βarr1ct has the amino acid sequence of SEQ ID NO:3.

The invention provides compositions for treatment of hyperaldosteronic conditions including a protein inhibitor of adrenal β-arrestin 1 (βarr1).

The invention provides compositions for treatment of hyperaldosteronic conditions including a βarr1 protein fragment comprising a C-terminus of βarr1 (βarr1ct). Particularly, βarr1ct has the amino acid sequence of SEQ ID NO:3.

The invention provides a method for treatment of a hyperaldosteronic condition in a patient comprising inhibiting adrenal via adrenal β-arrestin 1 (βarr1) and a therapeutically effective amount of a sartan. Particularly, the inhibitor can have the amino acid sequence of SEQ ID NO:3; the sartan can be candesartan or valsartan; and the hyperaldosteronic condition is chronic heart failure or heart failure progression post-myocardial infarction (MI).

The invention provides a method for inhibiting adrenal β-arrestin 1 (βarr1) in a patient having a hyperaldosteronic condition comprising overexpressing a βarr1 protein fragment comprising a C-terminus of βarr1 (βarr1ct). Particularly, the hyperaldosteronic condition is chronic heart failure or heart failure progression post-myocardial infarction (MI) and the βarr1ct has the amino acid sequence of SEQ ID NO:3.

The invention provides a method for inhibiting adrenal β-arrestin 1 (βarr1) in a patient having a hyperaldosteronic condition comprising administering an inhibitor of βarr1 and a therapeutically effective amount of a sartan to the patient. Particularly, the inhibitor can have the amino acid sequence of SEQ ID NO:3; the sartan can be candesartan or valsartan; and the hyperaldosteronic condition is chronic heart failure or heart failure progression post-myocardial infarction (MI).

The invention provides a method for attenuating progression of heart failure after myocardial infarction (MI) in a patient comprising administering an inhibitor of βarr1 and a therapeutically effective amount of a sartan to the patient. Particularly, the inhibitor can have the amino acid sequence of SEQ ID NO:3 and the sartan can be candesartan or valsartan.

The invention provides methods and compositions for fully blocking AngII-induced adrenal aldosterone production by inhibiting both the adrenalcortical βarr1 activation by AngII and the inhibition of G-protein activation by AngII.

In another embodiment, the invention provides an $AT_1R$-biased agonist for stimulating βarr1. Particularly, the ATA-biased agonist is an Ang II peptide analog having the amino acid sequence of SEQ ID NO:4.

The invention provides compositions comprising an $AT_1R$-biased agonist for stimulating βarr1. Particularly, the $AT_1R$-biased agonist is an Ang II peptide analog having the amino acid sequence of SEQ ID NO:4.

The invention provides a method for increasing angiotensin II-dependent β-arrestin activity in a patient comprising administering a therapeutically-effective amount of an angiotensin II (AngII) biased agonist to the patient, wherein the AngII agonist is an AngII peptide analog. Particularly, the Ang II peptide analog has the amino acid sequence of SEQ ID NO:4

The invention provides a method for increasing aldosterone production comprising administering an angiotensin II (AngII) biased agonist. Particularly, the Ang II biased agonist is an AngII peptide analog. Particularly, the Ang II peptide analog has the amino acid sequence of SEQ ID NO:4

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

A more complete understanding of the present invention may be obtained by references to the accompanying figures, when considered in conjunction with the subsequent detailed description. The embodiments illustrated in the figures are intended only to exemplify the invention and should not be construed as limiting the invention to the illustrated embodiments.

FIG. 5 shows the cardiac contractility of adrenal βarr1-overexpressing post-MI rats treated with sartans and CORET:

FIG. 6 shows the ranking of biased antagonism of sartans for $AT_1R$-stimulated βarr vs. G-protein-mediated signaling;

FIG. 7A shows a schematic representation of the βarr1 molecule;

FIG. 7B shows representative immunoblots for ERK2 phosphorylation and Steroidoegenic Acute Regulatory protein (StAR) and immunoblots for βarr1ct confirming transgene expression and for endogenous βarr1 showing no effects on endogenous βarr1 levels after adenoviral transfection;

FIG. 8A shows western blotting for adrenal StAR in AdGFP-, Ad βarr1-, or βarr1ct-treated two-week post-MI rats;

FIG. 8B shows the densitometric analysis for the blots of FIG. 8A;

FIG. 9 shows regulation of plasma aldosterone levels by adrenal βarr1, plasma aldosterone levels in AdGFP-Ad βarr1-, or Adβarr1ct-treated two-week post-MI rats;

FIGS. 10A-F show the effect of adrenal βarr1-mediated hyperaldosteronism on cardiac function, dimensions, and contractility;

FIG. 11 shows plasma aldosterone in AdGFP (saline-treated) and in Adβarr1-treated post-MI rats;

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described methods, therapeutic strategies, proteins, and any further application of the principles of the invention as described herein, are contemplated as would normally occur to one skilled in the art to which the invention relates.

Example I

Biased Agonism/Antagonism of β-Arrestin Activation by the Angiotensin Type 1 Receptor: A Study of Sartans and Angiotensin II Analogs Using Aldosterone Turnover as a Readout This experiment was carried out to (a) investigate the relative potency of various $AT_1R$ antagonist drugs, i.e. sartans, at inhibiting βarr1 vs. G-protein activation and hence aldosterone production in vitro and in vivo; (b) test novel AngII "biased" agonist analogs, i.e. analogs that only stimulate βarrs and not G-proteins, at stimulating βarr activity and aldosterone production; and (c) investigate the alterations in plasma aldosterone levels conferred by these agents (sartans and AngII biased agonist analogs) and their impact on cardiac function in post-myocardial infarction (MI) rats.

Methods

In vitro tests: For the in vitro tests, the adrenocortical H295R cell line was used, which produces aldosterone in response to AngII (Rainey, W. E. et al. *Mol. Cell. Endocrinol.* 228:23-38 2004).

In vivo studies: For the in vivo studies, post-MI rats overexpressing Purl in their adrenals received 7-day-long treatments with the agents of interest.

Aldosterone measurements: Plasma aldosterone and in vitro aldosterone secretion in the supernatant of cultured H295R cells were determined by ELISA with the Aldosterone EIA kit from ALPCO Diagnostics, Salem, N.H. (Lymperopoulos A. et al. *Proc. Natl. Acad. Sci. USA* 106:5825-5830 2009).

In vivo adrenal gene deliveries: Adrenal-specific in vivo gene delivery in rats was performed as previously described in Lymperopoulos A. et al. *Proc. Natl. Acad. Sci. USA* 106:5825-5830 2009).

Echocardiographic and hemodynamic measurements: Two-dimensional guided M-mode and Doppler echocardiography and closed chest cardiac catheterization were performed as described in Lymperopoulos, A. et al. *Nat. Med.* 13:315-323 2007.

Statistical analysis: Data are presented as mean±SEM. One- or two-way ANOVA with Bonferroni test was used for analysis of numeric parameters and differences were considered significant at p<0.05.

Experimental Results

The experimental results are shown in a series of figures, FIGS. 1A-C-FIG. 6.

Figure 1A:
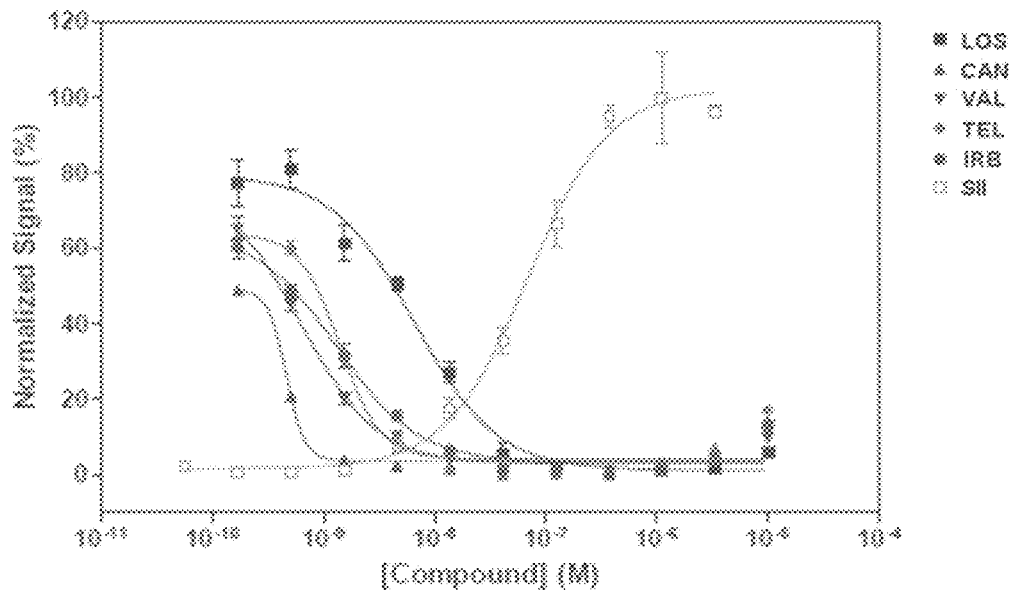
FIGS. 1A-C show the potency of sartans and AngII peptide analogs at inhibiting (FIG. 1A) or stimulating βarr activation (FIGS. 1B-C) by the human $AT_1R$.
Figure 1B:
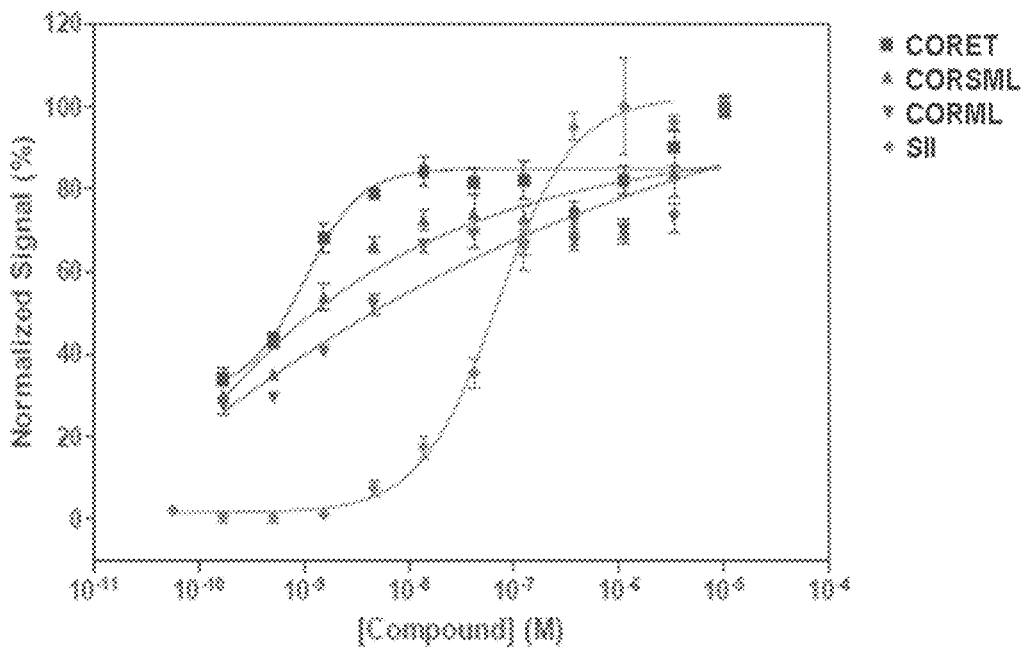
Figure 1C:
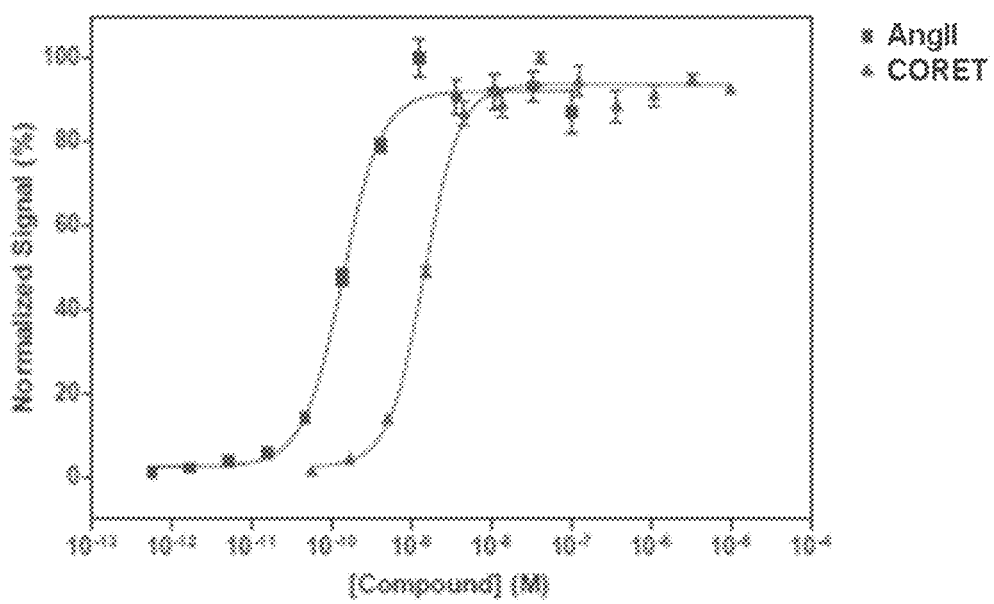

FIGS. 1A-C show the potency of sartans and AngII peptide analogs at inhibiting (or stimulating, respectively) βarr activation by the human $AT_1R$.

FIG. 1A demonstrates the relative potency of sartans for inhibition of SII (Sar$^1$,Ile$^4$,Ile$^8$-AngII)-induced activation of βarr2 by human $AT_1R$ in vitro. CAN & VAL appear the most potent inhibitors; i.e. they produce the lowest βarr2 activation, a % normalized signal). Abbreviations used in FIG. 1A are: LOS: Losartan, CAN: Candesartan, VAL: Valsartan, TEL: Telmisartan, IRB: Irbesartan.

FIG. 1B demonstrates the relative potency of some novel AngII peptide analogs for activation of βarr2 by human $AT_1R$ in vitro. These analogs are CORET: Sar$^1$,Cys(Et)$^5$, Leu$^8$-AngII (SEQ ID NO:4), CORSML: Sar$^1$,Met$^5$,Leu$^8$-AngII (SEQ ID NO (SEQ ID NO:15), CORML: Met$^5$,Leu$^8$-AngII (SEQ ID NO:16). CORET appears the most potent βarr agonist, with EC50 of 1 nM, vs. EC50 of 11.2 nM for SII.

FIG. 1C demonstrates that CORET (SEQ ID NO:4) is only 10 times less potent than AngII (the physiological endogenous agonist) for βarr activation by the $AT_1R$, with EC50s: 0.1 nM for AngII vs. 1 nM for CORET (SEQ ID NO:4).

Figure 2:
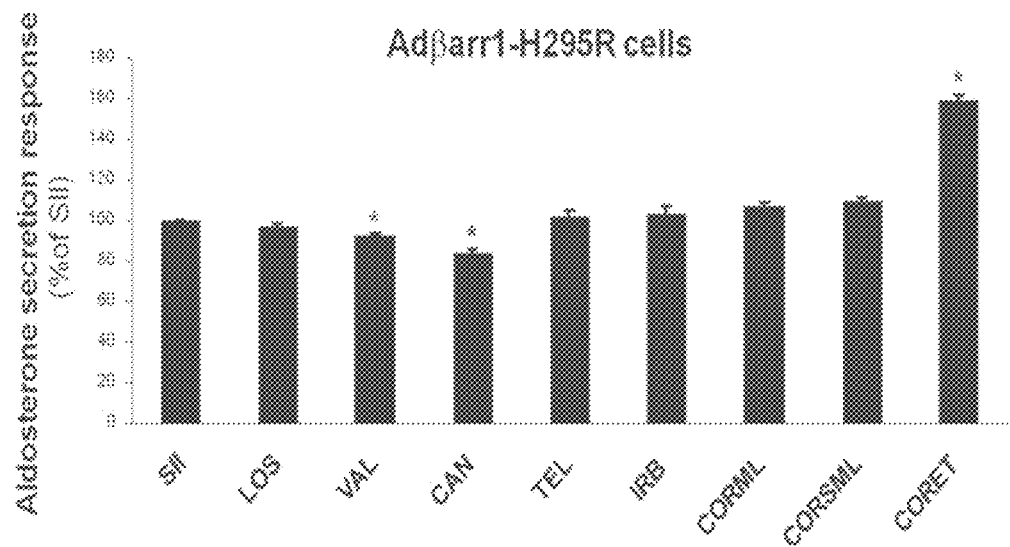
FIG. 2 shows in vitro βaa1-dependent aldosterone secretion response to sartans and AngII peptide analogs in H295 R cells.

FIG. 2 shows in vitro βarr1-dependent aldosterone secretion response to sartans and AngII peptide analogs in H295R cells.

FIG. 2 demonstrates the in vitro SII-induced aldosterone secretion response of H295R cells. The cells were transfected with adenovirus encoding for βarr1 (Adβarr1) to overexpress βarr1 and stimulated with 1 mM SII in the presence of standard doses of the sartans and the AngII peptide analogs. Consistent with the in vitro βarr stimulation data of FIGS. 1A-C, only CAN & VAL can inhibit and only CORET (SEQ ID NO:4) can enhance SII-induced aldosterone secretion statistically significantly in vitro. Of note, when endogenous Purl is inhibited, no effects by drugs and peptides on SII-induced aldosterone secretion are seen (data not shown), as expected, since SII is a "biased" βarr-only agonist (Luttrell, L. M. et al. *Pharmacol. Rev.* 62:305-330 2010; Rajagopal, S. et al. *Nat. Rev. Drug Discov.* 9:373-386 2010; Kenakin, T. et al. *Pharmacol. Rev.* 62:265-304 2010). Statistical analysis: <0.05, vs. SII, n=3 independent experiments.

Figure 3:
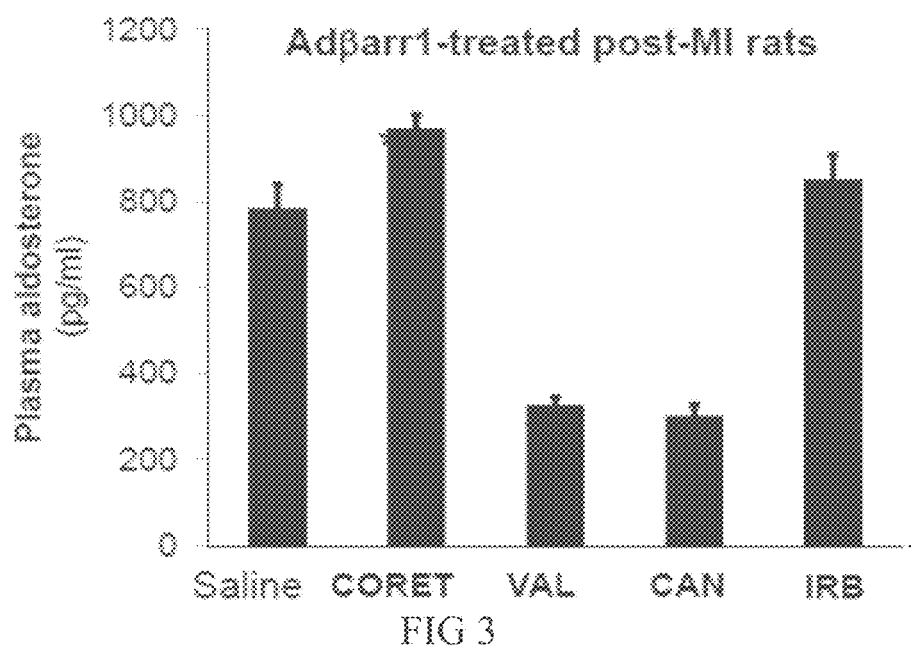
FIG. 3 shows plasma aldosterone in adrenal βarr1-overexpressing post-MI rats treated with sartans and CORET.

FIG. 3 shows plasma aldosterone in adrenal βarr1-overexpressing post-MI rats treated with sartans and CORET (SEQ ID NO:4).

FIG. 3 demonstrates plasma aldosterone levels in 3-week post-MI rats 7 days post-in vivo adrenal-specific adenoviral-mediated gene transfer of full-length wild type βarr1 (Adβarr1), and simultaneously treated with the indicated agents (or vehicle, Saline) for the same time-period (i.e. for the 7 days of post-gene delivery). CAN & VAL cause profound decreases in plasma aldosterone levels post-MI, whereas CORET (SEQ ID NO:4) causes an increase in plasma aldosterone levels on top of that normally present due to the post-MI HF progression. IRB, in marked contrast to CAN & VAL, appears unable to counter the adrenal βarr1-mediated hyperaldosteronism post-MI. Statistical analysis: p<0.05, vs. Saline, n=6 rats/group.

Figure 4:
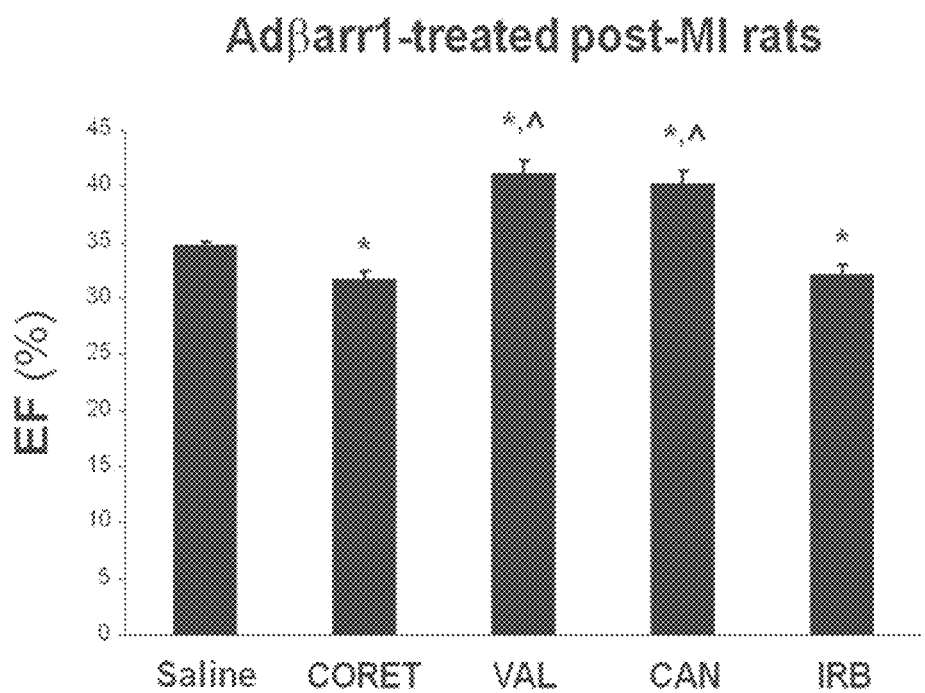
FIG. 4 shows the cardiac ejection fraction of adrenal βarr1-overexpressing post-MI rats treated with sartans and CORET.
Figures 12A, 12C:
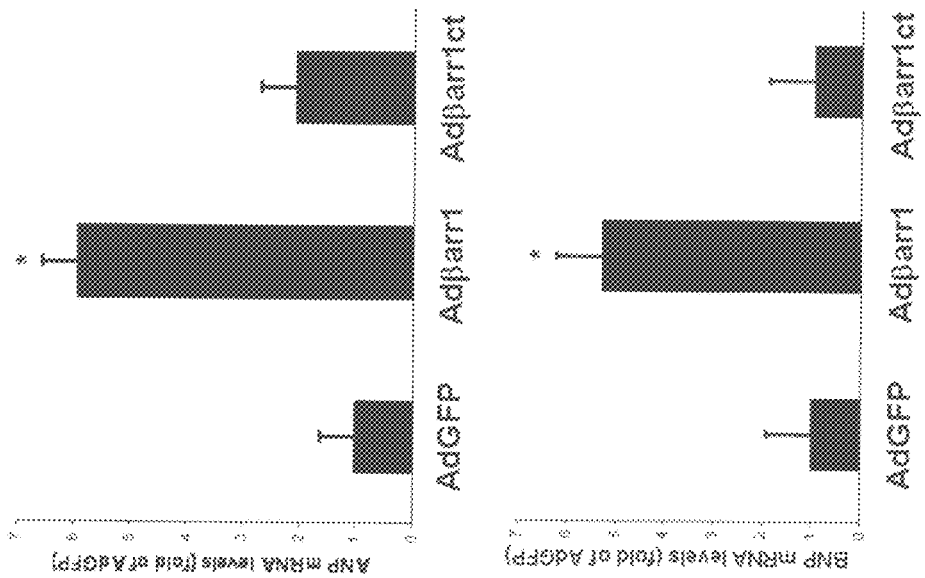
FIGS. 12A-D show the effect of aldosterone levels on cardiac remodeling markers.
Figures 12B, 12D:
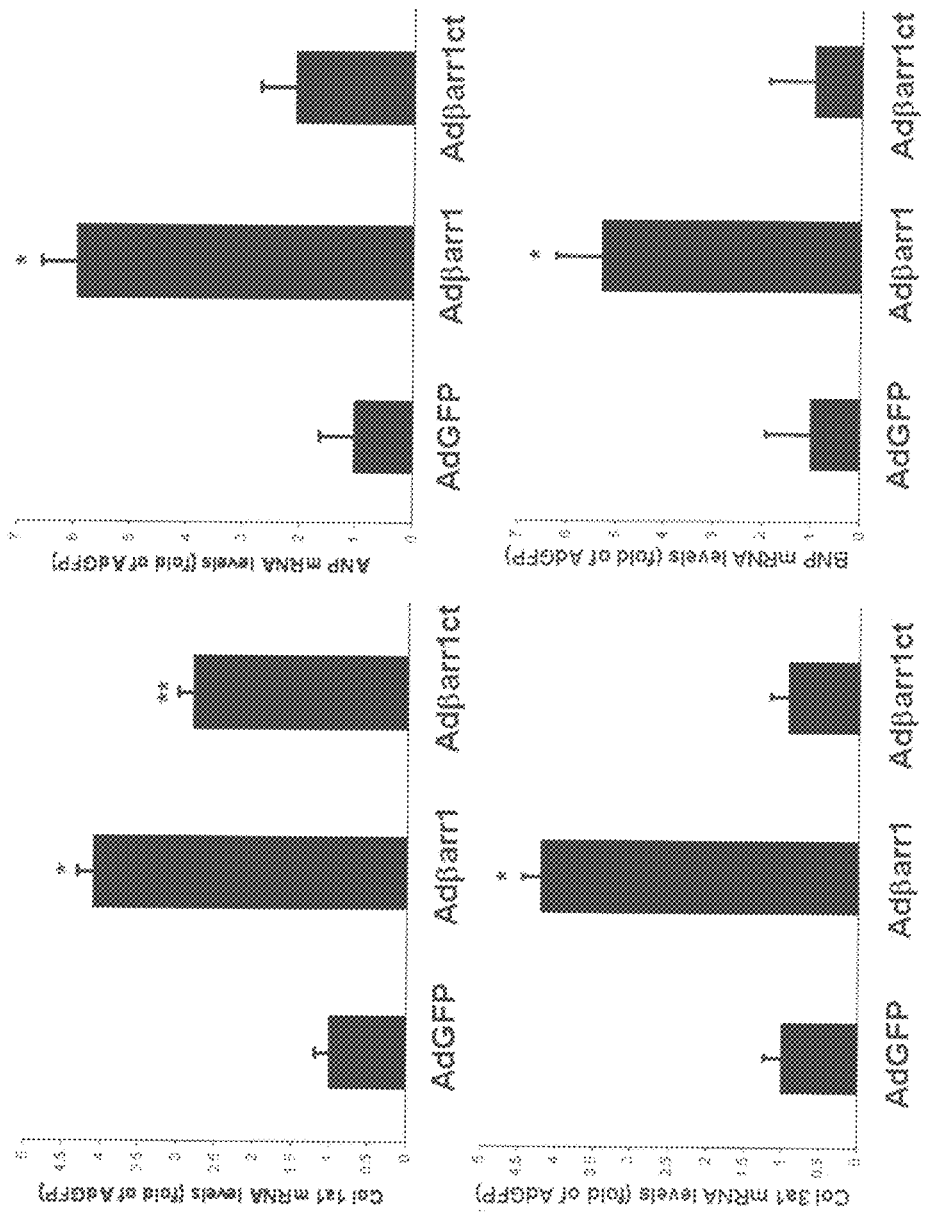

FIG. 4 shows cardiac ejection fraction (EF) of adrenal βarr1-overexpressing post-MI rats treated with sartans and CORET (SEQ ID NO:4).

FIG. 4 shows an echocardiographic analysis of 3-week post-MI rats at 7 days post-in vivo adrenal-specific gene transfer of Adβarr1 and concomitant treatment with the indicated agents, showing that ejection fraction (EF %) of post-MI rats treated with CAN or VAL significantly improved over control, non-treated (Saline) rats. In contrast, treatment with IRB or the peptide CORET (SEQ ID NO:4) further worsened cardiac function over the 7-day post-gene delivery period, consistent with the non-improvement and/or deterioration of post-MI hyperaldosteronism observed in FIG. 3 with these agents. Statistical analysis: p<0.05, vs. Saline, ˆ, p<0.05, vs. CORET (SEQ ID NO:4) or IRB, n=6 rats/group.

FIG. 5 shows cardiac contractility of adrenal βarr1-overexpressing post-MI rats treated with sartans and CORET (SEQ ID NO:4).

FIG. 5 shows an in vivo hemodynamic analysis of the post-MI adrenal βarr1-overexpressing rats treated with the indicated agents, showing that, consistent with the echocardiographic data of FIG. 4, animals treated with CORET (SEQ ID NO:4) or IRB display severely impaired myocardial systolic function in response to a maximal dose of the standard inotropic agent Isoproterenol (Max. Iso). Conversely, treatment with CAN or VAL significantly improves it. Statistical analysis: p<0.05, vs. Saline, ˆ, p<0.05, vs. CORET (SEQ ID NO:4) or IRB, n=6 rats/group.

FIG. 6 shows the ranking of "biased" antagonism of sartans for ATA-stimulated βarr vs. G protein-mediated signaling.

FIG. 6 shows the ranking of "bias" of the tested sartan drugs for antagonism of $AT_1R$-activated βarrs vs. G-proteins. This ranking was derived from the ratios of individual $IC_{50}$ for $AT_1R$-βarr antagonism to $IC_{50}$ for G-protein antagonism (both in nM) for each sartan. The closer to zero this ratio is (i.e. the more left it "falls" on the scale-line above), the more selective (biased) for βarr antagonism the drug is (e.g. CAN or VAL). The bigger than 1.0 the ratio is (i.e. the more right on the line above), the more biased towards G-protein antagonism the drug is (e.g. LOS). Ratio equal (or close) to 1.0 means no bias between the two signaling modalities (e.g. TEL or IRB). Ratio values calculated: CAN: 0.14, VAL: 0.23, TEL: 0.95, IRB: 1.05, LOS: 2.45.

Discussion Resulting from the Experiments of Example I

Among the sartans tested, candesartan and valsartan were the most potent βarr activation and βarr-mediated aldosterone production inhibitors in vitro, as well as the most biased antagonists towards βarr vs. G-protein inhibition. Conversely, losartan and irbesartan were the least potent βarr inhibitors and the least biased antagonists towards βarr inhibition. These in vitro findings were corroborated in vivo, since candesartan and valsartan, contrary to irbesartan, caused significant plasma aldosterone reductions in post-MI rats. The reduction in plasma aldosterone had an ameliorating effect on cardiac function in post-MI HF (heart failure) progression. This failure of irbesartan to improve post-MI adrenal βarr 1-dependent hyperaldosteronism, and hence cardiac function, might partly explain why this drug does not improve outcomes in heart failure patients with a preserved ejection fraction (EF) (Massie, B. M. et al. New England Journal of Medicine 359:2456-2467 2008).

Accordingly, cardiac ejection fraction (EF) and contractility were significantly augmented in candesartan- and valsartan-treated rats (EF: 41.1±1% and 40±1% respectively, vs. 35±0.3% for saline-treated), but further deteriorated in irbesartan-treated post-MI rats (EF: 32±1%, n=7 rats/group).

A novel $AT_1R$-biased agonist was identified, CORET ([Sar$^1$,Cys(Et)$^5$,Leu$^8$]-AngII; SEQ ID NO:4). CORET is far more potent at stimulating βarr than SII, the standard $AT_1R$-biased agonist (Luttrell, L. M. et al. Pharmacol. Rev. 62:305-330 2010; Rajagopal, S. et al. Nat. Rev. Drug Discov. 9:373-386 2010; Kenakin, T. et al. Pharmacol. Rev. 62:265-304 2010). Additionally, CORET produces far greater aldosterone secretion in vitro than SII, and significantly worsens hyperaldosteronism and cardiac function of post-MI rats in vivo. It is contemplated that CORET may be used, for example, as either a research tool to boost angiotensin-II-dependent β-arrestin activity in areas of research where this is a desirable outcome or as a therapeutic agent in cases where angiotensin-II-dependent β-arrestin activity is beneficial for cardiovascular health and hence β-arrestin activation would be therapeutically desirable.

Example II

Adrenal β-Arrestin 1 Inhibition In Vivo Attenuates Post-Myocardial Infarction (MI) Progression to Heart Failure (HF) and Adverse Remodeling Via Reduction of Circulating Aldosterone Levels Considering that Experimental Example I demonstrates that adrenal βarr1 promotes $AT_1R$-dependent aldosterone production leading to elevated circulating aldosterone levels in vivo, this experiment builds on these results and sought to investigate the potential role played by adrenal βarr1 in modulation of in vivo post-MI HF aldosterone levels.

Methods

Overview of Method: Adrenal-targeted, adenoviral-mediated gene delivery in vivo in two-week post-MI rats, a time point around which circulating aldosterone significantly increases to accelerate progression of heart failure, was performed to either increase the expression of adrenal βarr1 or inhibit its function via expression of a Pal C-terminal-derived peptide fragment (SEQ ID NO:3).

In vivo adrenal gene delivery in post-myocardial infarction (MI) rats: All animal procedures and experiments were performed in accordance with the guidelines of the IACUC committees of Thomas Jefferson and Nova Southeastern Universities. MI was performed using a known cryo-infarct method (Lymperopoulos, A. et al. Nat. Med. 13:315-323 2007). Adrenal-specific in vivo gene delivery was done essentially as described in Lymperopoulos, A. et al. (Mol. Ther. 16:302-307 2008) via direct delivery of adenovirus in the adrenal gland. Drug treatments were performed with 50 mg/kg/day of losartan potassium (in drinking water) and 100 (or 5) mg/kg/day eplerenone (both drugs obtained from Sigma-Aldrich, USA).

Construction and purification of adenovirus: Recombinant adenovirus that encode full length wild-type βarr1 (Adβarr1; SEQ ID NO:1) or a rat βarr1 C-terminal fragment (Adβarr-1ct) (SEQ ID NO:3, amino acid residues 369-418 of the C-terminal of rat βarr-1 (SEQ ID NO:2); see FIG. 7A) were constructed as described in Lymperopoulos A. et al. Proc. Nati. Acad. Sci. USA 106:5825-5830 2009 and Lymperopoulos, A. et al. Nat. Med. 13:315-323 2007. FIG. 7A shows a schematic representation of the βarr1 molecule highlighting its regulatory and functional domains, including the region covered by the βarr1ct peptide (SEQ ID NO:3, amino acid residues 369-418 of rat βaa1) used in the experiments described herein to limit βarr1 activity. The black box highlights the clathrin- and AP-2 adaptin-binding domains, which are necessary for the receptor internalizing and signaling functions of βarr1 (Ferguson, S. S. Pharmacol Rev 53:1-24 2001) Transgenes were cloned into shuttle vector pAdTrack-CMV, which harbors a CMV-driven green fluorescent protein (GFP), to form the viral constructs by using standard cloning protocols. As control adenovirus, empty vector which expressed only GFP (AdGFP) was used. The resultant adenovirus were purified using two sequential rounds of CsCl density gradient ultracentrifugation as described in Lymperopoulos A. et al. *Proc. Natl. Acad. Sci. USA* 106:5825-5830 2009 and Lymperopoulos, A. et al. *Nat. Med.* 13:315-323 2007.

Plasma aldosterone measurements: Rat plasma aldosterone levels were determined by EIA (Aldosterone EIA Kit, ALPCO Diagnostics, Salem, N.H., USA) as described in Lymperopoulos A. et al. *Proc. Natl. Acad. Sci. USA* 106: 5825-5830 2009 and Mihailidou et al. *Hypertension* 40:124-129 2002.

Echocardiographic and hemodynamic measurements: Two-dimensional guided M-mode and Doppler echocardiography using a 14-Mhz transducer (Vevo 770 Echograph, Visual-Sonic Inc., Toronto, Ontario, Canada) and closed chest cardiac catheterization were performed in rats as described in Lymperopoulos, A. et al. *Nat. Med.* 13:315-323 2007 and Rengo, G. et al. *Circulation* 119:89-98 2009. Three independent echocardiographic measurements were taken in both modes.

Western Blotting: Western blots to assess protein levels of Steroidogenic Acute Regulatory protein (StAR) (sc-25806), cardiac levels of PAI-1 (sc-8979), TGF-$\beta$1 (sc1460), $\beta$arr1 transgenes (A1CT antibody, a generous gift from Dr. R. J. Lefkowitz, Duke University Medical Center, Durham, N.C., USA) and GAPDH (MAB374; Chemicon, Temecula, Calif., USA) were done using protein extracts from rat adrenal glands or hearts as described in Lymperopoulos A. et al. *Proc. Natl. Acad. Sci. USA* 106:5825-5830 2009 and Lymperopoulos, A. et al. *Nat. Med.* 13:315-323 2007. Visualization of western blot signals was performed with Alexa Fluor 680- (Molecular Probes) or IRDye 800CW-coupled (Rockland, Inc.) secondary antibodies on a Ll-COR infrared imager (Odyssey).

Real-time PCR: Total heart RNA isolation, reverse transcription, and real-time RT-PCR were carried out as described in Lymperopoulos, A. et al. *Nat. Med.* 13:315-323 2007 and Rengo, G. et al. *Circulation* 119:89-98 2009. The following primer pairs were used: 5'-GTCCACGAGGT-GACAAAGGT-3' (SEQ ID NO:5) and 5'-CATCTTTTCCA-GGAGGTCCA-3' (SEQ ID NO:6) for Col3α1, 5'-CAC-CCCTTCTGCGTTGTATT-3' (SEQ ID NO:7) and 5'-TTGACCCTAACCAAGGATGC-3' (SEQ ID NO:8) for Col1α1, 5'-TGCCTGCACCTTTGTGATATCG-3' (SEQ ID NO:9) and 5'-CATGGCAGGACAATCGAACC-3' (SEQ ID NO:10) (NPR-B) for BNP, 5'-CATCCTGGACAACCTGC-3' (SEQ ID NO:11) and 5'-TAGGTCCGAACCTTGCC-3' (SEQ ID NO:12) (NPR-A) for ANP, and, finally, 5'-TCAAGAACGAAAGTCGGAGG-3' (SEQ ID NO:13) and 5'-GGACATCTAAGGGCATCAC-3' (SEQ ID NO:14) for 18S rRNA. Real time RT-PCR was performed using SYBR® Green Supermix (Bio-Rad). Normalization was done with 18S rRNA levels. No bands were seen in the absence of reverse transcriptase.

Masson-Trichrome staining: Masson-trichrome staining was performed as described in Shibata, R. et al. *Nat. Med.* 10:1384-1389 2004.

Statistical analysis: Data are generally expressed as mean±SEM. Unpaired 2-tailed Student's t test and one- or two-way ANOVA with Bonferroni test were generally performed for statistical comparisons, unless otherwise indicated. For most 3-group statistical comparisons Dunnett's test using SAS version 8.2 software was used. For all tests, a p value of <0.05 was generally considered to be significant.

Experimental Results
Summary of Results:

It was found that adrenal $\beta$arr1 overexpression promotes aldosterone elevation post-MI, resulting in accelerated cardiac adverse remodeling and deterioration of ventricular function. These detrimental effects of aldosterone are prevented when adrenal $\beta$arr1 is inhibited in vivo, which markedly decreases circulating aldosterone post-MI. The prototypic $AT_1R$ antagonist losartan appears unable to lower this adrenal $\beta$arr1-driven aldosterone elevation.

Adrenal $\beta$Arr1 and Post-MI Aldosterone Levels:

As noted above, this experiment was concerned with the potential role played by adrenal $\beta$arr1 in modulation of in vivo post-MI heart failure aldosterone levels. To this end, wild-type $\beta$arr1 (SEQ ID NO:2) or a $\beta$arr1 C-terminal fragment ($\beta$aa1ct; SEQ ID NO:3) was overexpressed, specifically in the adrenal glands of two-week post-MI rats. The $\beta$arr1ct (SEQ ID NO:3) is unable to bind receptor substrates and thus acts as an inhibitor of $\beta$arr1 scaffolding/signaling activity. To confirm the inhibitory effects of $\beta$arr1ct on $\beta$arr1 activity in vitro, an extensive molecular characterization of its effects on Angiotensin II (AngII)-induced signaling to aldosterone production in the human adrenocortical zona glomerulosa (AZG) cell line H295R was performed (FIG. 7B). $\beta$arr1ct was indeed found to abrogate $\beta$arr1- and G-protein-mediated signaling from ATiR to ERK activation and StAR up-regulation (FIG. 7B), both of which signaling events are absolutely necessary for AngII-driven aldosterone production and secretion from these adrenocorticol cells (Lymperopoulos A. et al. *Proc. Nati. Acad. Sci. USA* 106: 5825-5830 2009). This data is shown in the figures. FIG. 7B shows representative immunoblots for ERK2 phosphorylation and Steroidoegenic Acute Regulatory protein (StAR) in protein extracts from vehicle- and 100 nM AngII-treated H295R cells, transfected either with Ad $\beta$arr1ct or with control AdGFP adenovirus, including blots for total ERK1/2 and GAPDH as loading controls for phospho-ERK2 and StAR, respectively. Blots for $\beta$arr1ct confirming transgene expression and for endogenous $\beta$arr1 showing no effects on endogenous $\beta$arr1 levels after adenoviral transfection are also shown in FIG. 7B. Blots presented are representative of three independent experiments.

After confirming that $\beta$arr1ct acts as an inhibitor of adrenal $\beta$arr1-mediated aldosterone production in vitro, either the full length $\beta$arr1, SEQ ID NO:2 (to increase adrenal $\beta$arr1 levels/activity) or the $\beta$arr1ct, SEQ ID NO:3 (to inhibit adrenal $\beta$arr1 activity in vivo) was overexpressed in the adrenals of the post-MI rats. Experimental animals were randomized to three different groups: one group receiving adrenal gene transfer of AdGFP (control group), one group receiving full length wild type $\beta$arr1 (Ad $\beta$arr1), and one group receiving the $\beta$arr1ct (Ad$\beta$arr1ct). One day before adrenal gene transfer, all groups were analyzed by echocardiography to confirm presence of similar levels of left ventricle (LV) dysfunction and heart failure (HF). All groups were then studied over the course of the following 7 days (i.e. up to 3 weeks post-MI).

In vivo expression of the respective transgenes in the adrenal glands of the animals at 7 days post-gene delivery was confirmed by Western blotting (FIGS. 8A-B). Of note, the adrenal-targeted gene transfer methodology employed results in no ectopic transgene expression (data not shown herein, Lymperopoulos, A. et al. *Mol. Ther.* 16:302-307 2008). As expected, plasma circulating aldosterone levels at 7 days post-gene delivery were found markedly elevated in control AdGFP-treated post-MI rats (470±20 pg/ml, ~2-fold of the aldosterone levels of normal AdGFP-treated rats;

Lymperopoulos A. et al. *Proc. Nati. Acad. Sci. USA* 106: 5825-5830 2009) compared to normal (i.e. sham-operated) AdGFP-treated rats, indicating marked MI-induced aldosterone elevation. Importantly, adrenal βarr1 overexpression resulted in an even more pronounced aldosterone level post-MI, on top of that normally present due to the occurrence of MI (845±150 pg/ml in βarr1-treated vs. 470±20 pg/ml in control AdGFP-treated post-MI rats, n=6, p<0.05). This data is shown in the figures; i.e. FIG. 9 shows regulation of plasma aldosterone levels by adrenal βarr1, plasma aldosterone levels in AdGFP-Adβarr1-, or Adβarr1ct-treated two-week post-MI rats, at 7 days post-in vivo gene delivery; *, p<0.05, vs. AdGFP, **, p<0.05 vs. Adβarr1, n=6 rats/group.

In contrast, levels in Adβarr1ct-treated rats (350±30 pg/ml, n=6, p<0.05 vs. AdGFP) were significantly lower than in control AdGFP-treated post-MI rats (FIG. 9). Aldosterone levels in post-MI AdGFP rats were similar to levels in saline-treated post-MI rats (data not shown herein) indicating an absence of non-specific effects of the adenovirus used on plasma aldosterone values.

Consistent with the above findings, βarr1 overexpression led to significant up-regulation of adrenal StAR protein, the most critical enzyme in adrenocortical biosynthesis of aldosterone (as well as that of other adrenal steroids) (Lymperopoulos A. et al. *Proc. Nati. Acad. Sci.* USA 106:5825-5830 2009) compared to control AdGFP-treated post-MI rats, indicating enhanced aldosterone synthesis in vivo, whereas overexpression of Adβarr1ct reduced adrenal StAR protein levels below the levels of the control rats (FIGS. 8A-B). FIG. 8A shows western blotting for adrenal StAR in AdGFP-, Ad βarr1-, or βarr1ct-treated two-week post-MI rats, at 7 days post-in vivo gene delivery. Blots for βarr1 and βarr1ct are also shown confirming the overexpression of the respective transgenes, and for GAPDH as a loading control. FIG. 8B shows the densitometric analysis. *, p<0.05, vs. AdGFP, **, p<0.05, vs. βarr1, n=6 rats/group; Taken together, these results indicate that adrenal βarr1 promotes post-MI-associated hyperaldosteronism, and inhibition of its activity reduces aldosterone production and plasma circulating aldosterone levels post-MI in vivo.

In Vivo Cardiac Function and Dimensions at 7 Days Post-Gene Delivery:

Next, the impact of the adrenal βarr1-mediated hyperaldosteronism on the post-MI myocardium was examined. The ejection fraction (EF) was found markedly reduced in Adβarr1-treated post-MI rats at 7 days post-gene delivery, compared to control AdGFP-treated post-MI rats (41.4±1.2% vs. 48.7±1.1%, respectively, n=7, p<0.05) (FIG. 10A). FIG. 10A shows the ejection fraction (EF %) of Adβarr1- and control AdGFP-treated post-MI rats pre- and post-gene delivery (also see Table 1) *, p<0.05, vs. AdGFP-post-gene delivery or AdGFP-pre-gene delivery, **, p<0.05, vs. AdGFP-pre-gene delivery, n=7 rats/group.

EF in both groups was similar before gene delivery, and EF of AdGFP-treated rats at 7 days post-gene delivery was slightly but significantly reduced compared to pre-gene delivery, as expected, given that cardiac function deteriorates over time after MI, although at 3 weeks post-MI (when post-gene delivery measurements were taken) there is limited dysfunction in this model (FIG. 10A). Previous studies have shown that this model in the rat does not lead to significant cardiac dysfunction before ~10 weeks post-MI (Rengo, G. et al. *Circulation* 119:89-98 2009). Furthermore, Left Ventricular End Diastolic Diameter (LVEDD), a marker of cardiac dimensions, was significantly increased in Adβarr1-treated rats at 3 weeks post-MI compared to control AdGFP post-MI rats, in which heart enlargement was less pronounces at 3 weeks post-MI (FIG. 10B). FIG. 10B shows Left Ventricular End Diastolic Diamenter (LVEDD) of the rats of FIG. 10A. *, p<0.05, vs. AdGFP-post-gene delivery or Ad βarr1-pre-gene delivery, n=7 rats/group. This indicates that adrenal βarr1 overexpression significantly accelerates the progression of cardiac hypertrophy by promoting aldosterone elevation post-MI. EF and LVEDD of saline-treated 3-week post-MI rats were similar to those of control AdGFP-treated post-MI rats at 7 days post-gene delivery, indicating the absence of non-specific effects of the adenoviral gene delivery on cardiac function (data not shown herein).

These adrenal βarr1-induced cardiac alterations are alosterone-mediated, i.e. due to the elevated aldosterone levels caused by adrenal βarr1 overexpression in vivo, since EF reduction and LVEDD increase are prevented (i.e. are similar to control AdGFP-treated rats) by treatment of post-MI Adβarr1 rats with the aldosterone antagonist eplerenone (FIGS. 10C-D). FIGS. 10C-D show the ejection fraction (EF %) and (FIG. 10D) Left Ventricular End Diastolic Diameter (LVEDD) of Adβarr1-treated post-MI rats administered either with saline (vehicle) or with eplerenone (Adβarr1-Eplerenone) for 7 days, at 1 week post-gene delivery (3 weeks post-MI). AdGFP post-MI rats (treated with the vehicle) are also shown at 1 week post-gene delivery (3 weeks post-MI) for comparisons. *, p<0.05, vs. either AdGFP or Adβarr1-Eplerenone, no significant difference between AdGFP and Ad βarr1-Eplerenone was observed at p<0.05, n-5 rats/group. Although this drug (eplerenone), as expected, has no effect on the plasma aldosterone increase caused by the Adβarr1 treatment of the adrenals of these post-MI animals (FIG. 11). FIG. 11 shows plasma aldosterone in AdGFP (saline-treated) and in Adβarr1-treated post-MI rats, administered either with saline (vehicle) or with 100 mg/kg/day eplerenone (Adβarr1-Eplerenone) for 7 days, at 1 week post-gene delivery (3 weeks post-MI). *, p<0.05, vs. AdGFP, NS, Not Significant at p=0.05, n=5 rats/group.

Eplerenone prevented the effects of adrenal βarr1 overexpression at two completely different doses (a high one, 100 mg/kg/d, FIGS. 10C-D, and a low one, 5 mg/kg/d, data not shown herein). Thus, the cardiac effects observed upon adrenal βarr1 overexpression are mediated by circulating aldosterone.

Hemodynamic analysis revealed that Adβarr1-treated post-MI rats exhibited significantly reduced basal and maximal dose of isoproterenol-induced cardiac contraction and relaxation indices, compared to control AdGFP-treated rats (FIGS. 10E-F). FIGS. 10E-F show basal and maximal dose of isoproterenol (Max. Iso)-stimulated+dP/dt$_{max}$ (FIG. 10E) and −dP/dt$_{min}$ (FIG. 10F) responses of Adβarr1- and control AdGFP-treated post-MI rats at 7 days post-adrenal gene delivery (see also Table 1). *, p=0.05, vs. AdGFP, n=7 rats/group. At this early post-MI time point, when cardiac dysfunction has not yet manifested as heart failure (HF), echocardiographic and hemodynamic parameters of Adβarr1ct-treated post-MI rats did not display statistically significant differences from those of control AdGFp-treated post-MI rats, as expected, although there was some trend towards functional improvement in the Adβarr1ct group (see Table 1 for complete in vivo cardiac functional parameters in all three post-MI groups at one week after gene delivery). These results show that the adrenal βarr1-mediated hyperaldosteronism results in significantly accelerated deterioration of function of the post-MI rat heart.

Cardiac Remodeling and Functional Biomarkers at 7 Days Post-Gene Delivery:

Molecular and structural evaluation of the post-MI rat hearts at 7 days post-gene delivery was performed. Consistent with the in vivo functional data, real time PCR in total mRNA isolated from these hearts showed a marked upregulation of collagen types 1α1 and 3α1, markers of cardiac fibrosis, and of ANP (Atrial Natriuretic Peptide) and BNP (B-type Natriuretic Peptide), markers of cardiac hypertrophy, in the post-MI hearts of Adβarr1-treated rats, compared to control AdGFP-treated animals (FIGS. 12A-D). FIGS. 12A-D show Heart mRNA levels of (FIG. 12A) collagen I (Col1α1); (FIG. 12B) collagen III (Col3α1); (FIG. 12C) atrial natriuretic peptide (ANP); and (FIG. 12D) brain natriuretic peptide (BNP) in all experimental groups at 7 days post-gene delivery (3 weeks post-MI). All values were standardized to amplified 18S rRNA. Data are presented as mean±SEM and plotted as fold of AdGFP values. *, p<0.05, vs. AdGFP or Adβarr1ct, **, p<0.05 vs. AdGFP, n=5 rat hearts/group. Conversely, upregulation of all these markers was prevented in Adβarr1ct-treated rats (FIGS. 12A-D), despite the fact this group did not show significant improvement in cardiac function, which is not surprising given the early post-MI time-point these measurements were taken at. Thus, lowering of circulating aldosterone levels by adrenal βarr1 inhibition in vivo causes a marked reduction in the expression of adverse remodeling-related genes, which might help halt the post-MI cardiac decline at later timepoints. Additionally, heart weight-to-body weight ratio measurements also confirmed the accelerated cardiac hypertrophy (i.e. enhanced at one week post-adrenal gene delivery, compared to control AdGFP-treated) displayed by Adβarr1-treated post-MI rats (Table 1, see also, FIG. 10B).

Figure 13A:
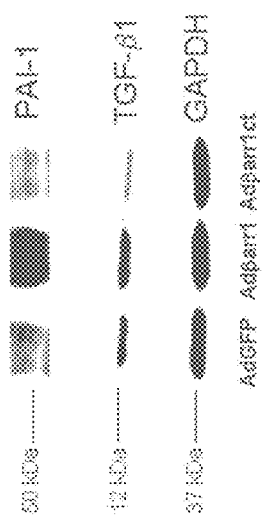
FIGS. 13A-E show the impact of aldosterone levels on cardiac fibrosis and adverse remodeling mediators.
Figure 13B:
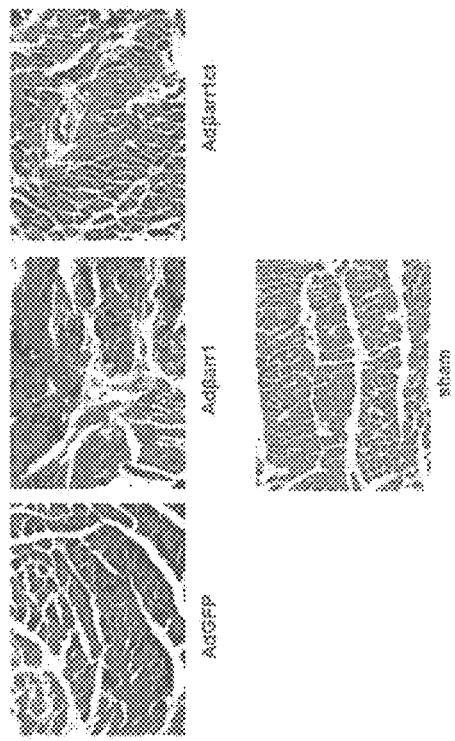
Figure 13C:
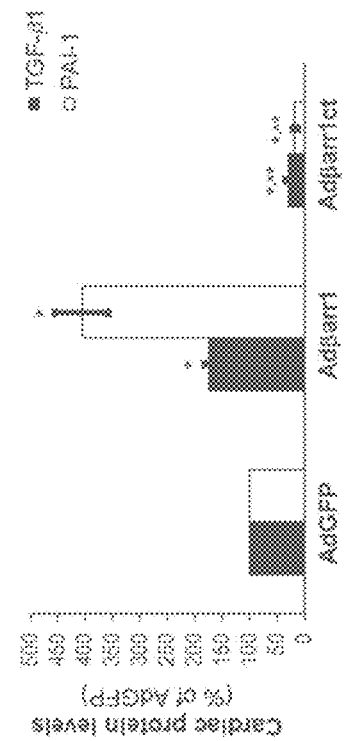
Figure 13D:
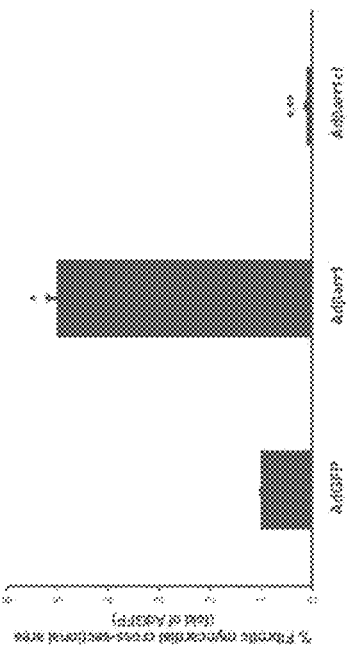
Figure 13E:

Cardiac Fibrosis at 7 Days Post-Gene Delivery:

Masson-trichrome staining for cardiac fibrosis at 3 weeks post-MI (7 days post-gene delivery) showed markedly increased fibrosis in Adβarr1-adrenal treated rat hearts compared to control AdGFP-treated rat hearts, whereas fibrosis was almost completely absent in Adβarr1ct-adrenal treated rat hearts (FIGS. 13A-B). FIG. 13A shows Trichrome-Masson's staining in myocardial cross-sections from AdGFP-, Adβarr1-, or Adβarr1ct-treated post-MI rats at 7 days post-adrenal gene delivery. Blue denotes collagen fibers, red denotes muscle fibers, and black represents cell nuclei. Representative images are shown from 5-6 rat hearts stained per group, along with staining in sham rat hearts, in which no blue staining was detectable. FIG. 13B shows quantification of the % fibrotic area visualized upon Trichrome-Masson's staining. *, p<0.05, vs. AdGFP, **, p<0.05 vs. Adβarr1, n=5-6 rat hearts/group. As expected, no fibrosis was detectable in sham-operated rat hearts (FIG. 13A). In addition, eplerenone treatment markedly reduced fibrosis in Adβarr1-adrenal treated rat hearts (FIG. 13E), thus providing another indication that the cardiac effects of βarr1 are aldosterone-dependent. FIG. 13E shows Trichrome-Masson's staining in myocardial cross sections from Adβarr1-treated post-MI rats at 7 days post-adrenal gene delivery, concomitantly administered either vehicle (saline), Losartan, or Eplerenone. Representative images are shown from 5-6 rat hearts stained per group.

(C) Western blotting for cardiac PAI-1 and TGF-β1 in AdGFP-, Adβarr1-, or Adβarr1ct-treated post-MI rats, at 7 days post-gene delivery, including GAPDH as loading control. (D) Densitometric analysis of 5 heart samples tested per group. *, p<0.05, vs. AdGFP, **, p<0.05 vs. Adβarr1, n=5 rat hearts/group.

Cardiac Mediators of Aldosterone at 7 Days Post-Gene Delivery:

Immunoblotting in cardiac protein extracts revealed a marked upregulation of cardiac Plasminogen Activator Inhibitor (PAI)-1 and Transforming Growth Factor-β (TGF-β), two of the most important molecular mediators of aldosterone's cardiac fibrotic and adverse remodeling actions (Marney, A. M. et al. Clin Sci (Loud) 113:267-278 2007) in the post-MI hearts of Adβarr1-treated rats compared to control AdGFP-treated rats (FIGS. 13C-D). FIG. 13C shows Western blotting for cardiac PAI-1 and TGF-β1 in AdGFP-, Adβarr1-, or Adβarr1ct-treated post-MI rats, at 7 days post-gene delivery, including GAPDH as loading control. FIG. 13D shows densitometric analysis of 5 heart samples tested per group. *, p<0.05, vs. AdGFP, **, p<0.05 vs. Adβarr1, n=5 rat hearts/group. In contrast, in the hearts of Adβarr1ct-treated rats, not only was upregulation of PAI-1 and TGF-β prevented, but the levels of these proteins were actually lowered below the levels of control AdGFP-treated rats (FIGS. 13C-D). Taken together, these results indicate that adrenal βarr1-mediated hyperaldosteronism accelerates cardiac adverse remodeling and progression to heart failure after myocardial infarction, and that these effects can be reciprocally mitigated by adrenal βarr1 inhibition, which significantly reduces circulating aldosterone levels.

Figure 14:
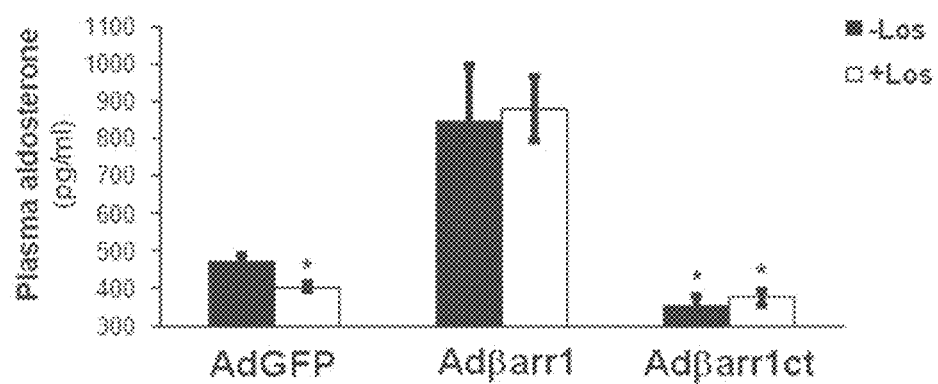
FIG. 14 shows plasma aldosterone levels 7 days post-adrenal gene delivery of post-MI rats after concomitant vehicle (−Los) or losartan (+Los) treatment.

Angiotensin Antagonism and βarr1-Mediated Aldosterone Levels Post-MI:

It was examined whether adrenal βarr1 can affect the efficacy of $AT_1R$ antagonism at curbing AngII-induced aldosterone production. For this purpose, post-MI rats were treated with the prototypic ATA antagonist losartan (McMurray, J. J. J Renin Angiotensin Aldosterone Syst 5(Suppl. 1):517-S22 2004; Diex, J. Clin Ther 28:832-848 2006) for the entire 7-day post-gene delivery period at a dose of 50 mg/kg/day. As expected, in control AdGFP-treated post-MI rats, losartan produced a small but significant plasma aldosterone reduction (from 470±20 in saline-treated to 402±10 pg/ml in losartan-treated rats, p<0.05, n=6) (FIG. 5). In Adβarr1-treated post-MI rats however, losartan is virtually unable to lower aldosterone levels (845±150 in saline-treated vs. 880±88 pg/ml in losartan-treated rats, Not Significant at p<0.05, n=6) (FIG. 13). In the Adβarr1ct-treated group, no significant aldosterone reduction by losartan was observed, probably because plasma aldosterone levels were already reduced below the levels of AdGFP-treated rats by Adβarr1ct alone. Consistent with this, losartan seems also incapable of reducing the cardiac fibrosis induced by adrenal βarr1-mediated hyperaldosteronism (FIG. 13E). However, levels in both the saline- and losartan-treated Adβarr1ct rats were significantly lower than in vehicle-administered control AdGFP post-MI rats (FIG. 14). FIG. 14 shows adrenal βarr1-dependent aldosterone levels and losartan; i.e. plasma aldosterone levels 7 days post-adrenal gene delivery of post-MI rats after concomitant vehicle (−Los) or losartan (+Los) treatment. *, p<0.05, vs. AdGFP/−Los or Adβarr1/+Los, n=5 rats/group/treatment. These results strongly suggest that losartan's post-MI aldosterone lowering effects are antagonized by adrenal βarr1, therefore, adrenal βarr1 inhibition can potentiate the hypoaldosteronic actions of this drug in post-MI HF. Effects of losartan in AdGFP-treated and saline-treated post-MI rats were similar (data not shown).

Discussion Resulting from the Experiments of Example II

Adrenal βarr1 promotes AngII-dependent aldosterone production in vitro in human adrenocortical zona glomerulosa (AZG) cells, independently of G-proteins (Lymperopoulos A. et al. *Proc. Natl. Acad. Sci. USA* 106:5825-5830 2009). Additionally, adrenal-specific βarr1 overexpression in vivo results in marked elevation of circulating aldosterone levels in otherwise normal animals (Lymperopoulos A. et al. *Proc. Natl. Acad. Sci. USA* 106:5825-5830 2009). These experiments (Example II) sought to investigate whether adrenal βarr1 plays any role in regulation of circulating aldosterone levels in post-myocardial infarction (MI) heart failure (HF) progression. It was found that adrenal βarr1 is indeed a crucial regulator of circulating aldosterone levels in vivo during post-MI HF progression, in that increased adrenal βarr1 levels/activity promotes aldosterone elevation post-MI, resulting in accelerated cardiac adverse remodeling and deterioration of function, whereas blockade of its activity in vivo lowers post-MI aldosterone levels, attenuating or even preventing these detrimental effects of aldosterone on the failing heart.

These findings presented herein strongly suggest that blockade of adrenal βarr1 action on $AT_1R$ might serve as a novel therapeutic strategy for lowering aldosterone levels post-MI and in heart failure. This is particularly important, since aldosterone has been shown to exert some of its actions (its so-called "non-genomic" actions) independently of the mineralocorticoid receptor (MR), its molecular target that normally mediates its cellular actions (Connel, J. M. et al. *Journal of Endocrinology* 186:1-20 2005; Marney, A. M. et al. *Clin Sci (Loud)* 113:267-278 2007). These MR-independent actions are unaffected by the currently available MR antagonists, such as eplerenone and spironolactone, used in the treatment of heart failure (Pitt, B. et al. *New England Journal of Medicine* 348:1309-1321 2003; Pitt, B. et al. *New England Journal of Medicine* 341:709-717 1999). Therefore, curbing aldosterone production at its major source, i.e. the adrenal cortex, by inhibiting βarr1 actions, could presumably be more effective therapeutically than inhibiting aldosterone's actions at its receptor level.

In addition, since adrenal βarr1 appears necessary for upregulation of Steroidogenic Acute Regulatory protein (StAR), the enzyme that regulates synthesis of all adrenal steroids, its inhibition presumably leads to suppression of the production of the other adrenocortical steroids as well, i.e. of glucocorticoids and corticosterone (Lymperopoulos A. et al. *Proc. Natl. Acad. Sci. USA* 106:5825-5830 2009). Of note, glucocorticoids have been reported to actually occupy the cardiac mineralocorticoid receptors (MRs) under normal conditions instead of aldosterone (Qin, W. et al. *Circ Res* 93:69-76 2003). Therefore, adrenal βarr1 inhibition, by suppressing production of glucocorticoids and mineralocorticoids alike, has the unique potential of keeping cardiac MRs completely at bay. For this very same reason, adrenal βarr1 emerges as a much superior target for post-MI cardiac remodeling and heart failure treatment than MR inhibition (e.g. with eplerenone) or aldosterone synthase inhibition, given that the latter strategies cannot counter all the adverse effects of all adrenal steroids post-MI, as suppression of all adrenal steroid production via adrenal βarr1 inhibition is projected to do.

Another important ramification of the present study is that pathological situations that cause elevation of adrenal βarr1 activity towards receptors can lead to abnormally high AngII-induced aldosterone production and hyperaldosteronism. Indeed, we recently reported that in chronic heart failure, adrenal GRK2, a protein kinase that induces receptor-βarr coupling, is dramatically upregulated resulting in chronically enhanced catecholamine production by the adrenal medulla (Lymperopoulos A. et al. *Nat. Med.* 13:315-323 2007). Thus, it is entirely plausible that, driven by the enhanced GRK2 activity, adrenal βarr1 activity towards receptors, including the $AT_1Rs$, is also increased in chronic HF or during progression from MI to HF, which could mediate (at least in part) the chronically elevated circulating levels of aldosterone that precipitate this disease. Importantly, it has been shown that GRK2 can desensitize AngII receptors in the heart in vivo (Rockman, H. A. et al. *Proceedings of the National Academy of Science USA* 93:9954-9959 1996), and that overexpression of GRK2 in rat adrenal glands also causes elevation of plasma aldosterone (Lymperopoulos A. et al. *Proc. Natl. Acad. Sci. USA* 106:5825-5830 2009). Both of these findings argue in favor of the aforementioned scenario.

Furthermore, it is now well established that, in addition to the circulatory renin-angiotensin-aldosterone system (RAAS), there are also several other local RAAS's in peripheral tissues, including the heart (intracardiac RAAS) and the kidneys (intrarenal RAAS), and these systems also hyperfunction in HF contributing to the HF-associated hyperaldosteronism (Kobori, H. et al. *Pharmacol Rev* 59:251-287 2007; Silvestre, J. S. et al. *Circ* 99:2694-2701 1999). Therefore, it would be worth investigating whether βarr1 is involved in aldosterone production by these local RAAS's, and whether it contributes to their increased aldosterone output during heart failure as well. In fact, specifically for the intracardiac RAAS, this possibility is very likely, given the elevated cardiac GRK2 levels in HF (Rockman, H. A. et al. *Nature* 415:206-212 2002).

One of the major physiological effects of aldosterone is an increase in blood pressure via salt and water retention (Connel, J. M. et al. *Journal of Endocrinology* 186:1-20 2005; Marney, A. M. et al. *Clin Sci* (Loud) 113:267-278 2007). Thus, alterations in mean arterial pressure by the elevated aldosterone levels caused by adrenal βarr1 overactivity might very well have contributed to the observed cardiac phenotype of adrenal βarr1-overexpressing post-MI rats. It should be noted here however that βarr1 knockout mice do not show any changes in blood pressure compared to wild type age-matched control mice (Conner, D. A. et al. *Circ Res* 81:1021-1026 1997). Additionally, the direct effects of aldosterone on cardiac tissue are bound to have played the most important role in the observed cardiac phenotype of the post-MI animals, given the relatively small time-period (only 7 days) between genetic manipulation of adrenal βarr1 levels which raises aldosterone levels (i.e. gene delivery) and the day of cardiac measurements/examination, which is rather insufficient for blood pressure to affect cardiac function and remodeling that dramatically. Besides, whether changes in blood pressure play any role in the cardiac effects of aldosterone is still an open question in its own right, since there are several reports in the literature showing aldosterone to affect cardiac function and fibrosis in post-MI rats independently of changes in mean blood pressure (Nehme, J. A. et al. *J Mol Cell Cardiol* 39:511-519 2005; Benetos, A. et al. *Arterioscler Thromb Vasc Biol* 17:1152-1156 1997). Indeed, no differences in systemic mean arterial pressure among the three post-MI treatment groups of the present study (i.e. AdGFP, Adβarr1, Adβarr1ct) were observed at one week post-gene delivery (data not shown), further supporting the notion that blood pressure did not play any major role in the observed cardiac effects of βarr1-dependent aldosterone at this early post-MI time-point (3 weeks).

The last finding of the present study is that the aldosterone-lowering actions of losartan, the prototypic drug of the class of $AT_{1A}R$ antagonists (sartans) (McMurray, J. J. *J Renin Angiotensin Aldosterone Syst* 5(Suppl. 1):S17-S22

2004; Diex, J. Clin Ther 28:832-848 2006), are countered by adrenal βarr1. Although at normal βarr1 levels (control AdGFP-treated post-MI rats) it is capable of producing a small but significant plasma aldosterone lowering as expected, when adrenal βarr1 is overactive (Adβarr1-treated post-MI rats), losartan does not decrease plasma aldosterone at all. This finding implies that inhibition of adrenal βarr1 in vivo can facilitate the inhibitory effects of losartan (and possibly also of the other sartans) on AngII-induced aldosterone production. Of note, limited efficacy of losartan and other sartans at lowering aldosterone levels in HF patients and in experimental animals, the so-called "aldosterone escape", has been reported (Mihailidou, A. S. et al. *Hypertension* 40:124-129 2002; Borgi, C. et al. *J Clin Pharamacol* 33:40-45 1993; Struthers, A. D. *Eur Heart J* 16(Suppl N):103-106 1995). Therefore, the finding that losartan's effects on aldosterone production can be antagonized by adrenal βarr1-ATA coupling might explain (at least in part) this reported limited efficacy of losartan and related drugs at curbing aldosterone levels. On the other hand, increased activity of the βarr1 co-factor GRK2 on cardiac $AT_1Rs$ also attenuates the pro-contractile signaling of these receptors (Rockman, H. A. et al. *Proceedings of the National Academy of Science USA* 93:9954-9959 1996). Therefore, the development of novel, functionally selective (or "biased") $AT_1R$ ligands (Violin, J. D. et al. *Trends Pharmacol Sci* 28:416-422 2007; Neubig, R. R. *Mol Pharmacol* 71:1200-1202 2007), which would inhibit $AT_1R$-induced GRK2/βarr1 activation, at least as effectively as $AT_1R$-induced G-protein activation, might prove extremely beneficial in the treatment of HF-related hyperaldosteronism and decreased cardiac function.

Clinical Implications of the Results

It was found that circulating aldosterone levels are reciprocally regulated by adrenal βarr1 activity in vivo, in that they are directly proportional to βarr1 activity toward AngII receptors in the adrenal glands. Therefore, inhibiting adrenal βarr1 action markedly decreases circulating aldosterone and attenuates its detrimental effects on the post-MI heart, such as fibrosis, hypertrophy, and dilatation, thereby preventing or even reversing adverse remodeling post-MI and maintaining cardiac function in the face of post-MI-driven cardiac decline. Additionally, losartan, a classical AngII receptor antagonist drug used in the treatment of hypertension, appears unable to counter this adrenal βarr1-promoted hyperaldosteronism post-MI. Taken together, the present findings suggest adrenal βarr1 as a major driving force behind post-MI aldosterone elevation, whose inhibition in vivo, either via gene therapy or pharmacologically, could potentially be of enormous therapeutic value in the management of post-MI heart failure patients. Finally, from the pharmacotherapeutic standpoint, an evaluation of the whole class of $AT_1R$ antagonists (sartans) in terms of their efficacy at antagonizing βarr1-driven hyperaldosteronism is highly warranted, as it could help explain some well-known existing differences in therapeutic efficacy, and also identify the most efficacious agents at lowering post-MI aldosterone, within this very important cardiovascular drug class.

In summary, the results demonstrate that adrenal βarr1 promotes the well-documented post-MI-associated elevation of circulating aldosterone, and thus, direct inhibition of its activity via adrenal-targeted gene therapy or via development of novel $AT_1R$ "biased" or "functionally selective" ligands that can prevent/reduce GRK2/βarr1 activation by the $AT_1R$ might be of therapeutic value in post-MI ensuing HF, as well as in already established chronic HF, both of which are precipitated by the cardiotoxic actions of elevated aldosterone.

Conclusion

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The proteins, peptides, nucleotides, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

TABLE 1

In vivo cardiac functional parameters after adrenal gene delivery

| | sham-operated (n = 6) | AdGFP (n = 7) | Adβarr1 (n = 7) | Adβarr1ct (n = 7) |
|---|---|---|---|---|
| Echocardiographic parameters after gene delivery | | | | |
| LVIDs (mm) | 3.76 ± 0.08 | 6.6 ± 0.04# | 7.2 ± 0.04#,* | 6.0 ± 0.04#,** |
| LVEDD (mm) | 6.36 ± 0.15 | 8.7 ± 0.25# | 9.5 ± 0.15#,* | 7.9 ± 0.5#,** |
| FS (%) | 37.09 ± 1.39 | 25.6 ± 0.7# | 21.3 ± 0.7#,* | 28.6 ± 2.7#,** |
| EF (%) | 65.01 ± 1.77 | 48.7 ± 1.1# | 41.4 ± 1.2#,* | 52.3 ± 2.9#,** |
| PWTd (mm) | 1.25 ± 0.08 | 1.6 ± 0.04# | 2.0 ± 0.2#,* | 1.4 ± 0.24#,** |
| Basal LV Hemodynamic Measurements | | | | |
| HR (min−1) | 354.2 ± 13.9 | 352.8 ± 16.2 | 363.6 ± 7.8 | 356.8 ± 14.2 |
| LV +dP/dt$_{max}$ (mm Hg/s) | 9,997 ± 446 | 7,549 ± 512# | 5,820 ± 88.5#,* | 8,149 ± 512#,** |
| LV −dP/dt$_{min}$ (mm Hg/s) | −8,598 ± 248 | −6,157 ± 392# | −5190 ± 110#,* | −6,657 ± 392#,** |
| LVESP | 120.6 ± 1.1 | 115.0 ± 4.7 | 104.2 ± 4.4#,* | 118.0 ± 3.7** |
| LVEDP | 1.7 ± 0.6 | 2.8 ± 0.4 | 8.2 ± 1.0#,* | 2.3 ± 0.4** |

TABLE 1-continued

In vivo cardiac functional parameters after adrenal gene delivery

|  | sham-operated (n = 6) | AdGFP (n = 7) | Adβarr1 (n = 7) | Adβarr1ct (n = 7) |
|---|---|---|---|---|
| Hemodynamic Measurements after maximal Isoproterenol (333 ng/kg BW) | | | | |
| HR (min−1) | 434.2 ± 13.2 | 437 ± 15.0 | 452 ± 13.0 | 447 ± 16.0 |
| LV +dP/dt$_{max}$ | 15,128 ± 391 | 11,200 ± 668[#] | 9,742 ± 291[#,*] | 11,900 ± 668[#,**] |
| LV −dP/dt$_{min}$ | −9,981 ± 115 | −7,509 ± 496[#] | −6,646 ± 171[#,*] | −8,209 ± 496[#,**] |
| LVESP | 127.9 ± 1.8 | 122.0 ± 4.9 | 111.2 ± 2.3[#,*] | 124.0 ± 4.6[**] |
| LVEDP | 1.9 ± 0.9 | 3.1 ± 0.4 | 8.8 ± 0.9[#,*] | 2.8 ± 0.4[**] |
| Phenotypic data: | | | | |
| HW/BW (mg/g) | 2.03 ± 0.16 | 2.7 ± 0.16[#] | 3.3 ± 0.21[#,*] | 2.5 ± 0.11[#,**] |

Adrenal gene delivery of AdGFP, Adβarr1 or Adβarr1ct was performed at 2 weeks post-myocardial infarction (MI) and the above parameters were measured 7 days post-gene delivery (direct adrenal gland injection).
Values of age-matched sham-operated animals are shown for comparisons.
LV +dP/dt$_{max}$, maximal first derivative of LV pressure rise;
LV −dP/dt$_{min}$, minimal first derivative of LV pressure fall;
HR, heart rate;
LVESP, LV end systolic pressure;
LVEDP, LV end diastolic pressure;
LVEDD, LV end-diastolic diameter;
LVIDs, LV inner diameter during systole;
FS, fractional shortening;
EF, ejection fraction;
PWTd, posterior wall thickness in diastole;
HW/BW: Heart weight-to-body weight ratio;
LV: Left ventricular;
[#]p < 0.05 vs. sham-operated,
[*]p < 0.05 vs. AdGFP,
[**]p < 0.05 vs. Adβarr1.
ANOVA with Bonferroni test was performed among all groups.
Data are presented as mean ± SEM.

What is claimed is:

1. A composition for attenuating progression of heart failure after myocardial infarction (MI) in a human patient, the composition comprising a human β-arrestin 1 (βarr1) protein fragment and a therapeutically-effective amount of a sartan.

2. The composition according to claim 1, wherein the sartan is candesartan or valsartan.

3. A method for attenuating progression of heart failure after myocardial infarction (MI) in a patient comprising administering the composition of claim 1 to the patient.

4. The method according to claim 3, wherein the sartan is candesartan or valsartan.

5. The method according to claim 4, wherein the composition is administered 2 weeks after the myocardial infarction (MI).

* * * * *